US012564706B2

(12) United States Patent
Arnett et al.

(10) Patent No.: US 12,564,706 B2
(45) Date of Patent: Mar. 3, 2026

(54) ENHANCED DILATOR AND METHODS OF USING THE SAME

(71) Applicant: Boston Scientific Medical Device Limited, Galway (IE)

(72) Inventors: Jeffery Arnett, Gilbert, AZ (US); David Rees, Toronto (CA)

(73) Assignee: Boston Scientific Medical Device Limited, Galway (IE)

( * ) Notice: Subject to any disclaimer, the term of this patent is extended or adjusted under 35 U.S.C. 154(b) by 328 days.

(21) Appl. No.: 18/185,515

(22) Filed: Mar. 17, 2023

(65) Prior Publication Data

US 2023/0364396 A1     Nov. 16, 2023

Related U.S. Application Data

(60) Provisional application No. 63/482,761, filed on Feb. 1, 2023, provisional application No. 63/320,957, filed on Mar. 17, 2022.

(51) Int. Cl.
A61M 29/00          (2006.01)

(52) U.S. Cl.
CPC .................................. A61M 29/00 (2013.01)

(58) Field of Classification Search
CPC .......... A61B 17/3478; A61M 25/0097; A61M 29/00; A61M 29/02
USPC ........................................................ 606/191
See application file for complete search history.

(56) References Cited

U.S. PATENT DOCUMENTS

| | | | | |
|---|---|---|---|---|
| 4,682,981 A | * | 7/1987 | Suzuki .............. | A61M 25/0097 604/533 |
| 2007/0038219 A1 | * | 2/2007 | Matthis .............. | A61B 17/8625 623/17.11 |
| 2019/0030294 A1 | * | 1/2019 | McLaughlin ......... | A61M 29/00 |
| 2019/0290403 A1 | * | 9/2019 | Thomke .............. | A61C 8/0012 |
| 2020/0060710 A1 | * | 2/2020 | Urbanski ........... | A61B 18/1492 |

FOREIGN PATENT DOCUMENTS

WO     WO-2019215623 A1 * 11/2019     ......... A61B 17/3421

OTHER PUBLICATIONS

International Search Report and Written Opinion issued in PCT/EP2023/056917, issued on Jul. 10, 2023, 13 pages.

* cited by examiner

*Primary Examiner* — Jocelin C Tanner
(74) *Attorney, Agent, or Firm* — Nelson Mullins Riley & Scarborough LLP

(57)          ABSTRACT

An enhanced dilator includes a dilator shaft defining a lumen for receiving a functional device (e.g., a puncturing device) therethrough. The dilator shaft includes a proximal portion for manipulation by a user and a distal portion to placement in or near the heart. A dilator hub is coupled to the proximal portion of the dilator shaft and includes a rotational coupling structure for coupling to a corresponding hub of a therapy sheath.

20 Claims, 21 Drawing Sheets

ENHANCED DILATOR AND METHODS OF USING THE SAME

CROSS REFERENCE TO RELATED APPLICATIONS

This application claims the benefit of U.S. Provisional Application No. 63/320,957, entitled "ENHANCED DILATOR AND METHODS OF USING THE SAME," and filed Mar. 17, 2022, and U.S. Provisional Application No. 63/482,761, entitled "ENHANCED DILATOR AND METHODS OF USING THE SAME," and filed Feb. 1, 2023, which are hereby incorporated by reference in their entireties.

TECHNICAL FIELD

The present invention relates generally to methods and devices usable to deliver a therapy to a patient. More specifically, the present invention is concerned with a system and method for delivering a therapy device to a heart.

BACKGROUND

Devices currently exist for creating a puncture, channel, or perforation within a tissue located in a body of a patient. One such device is the Brockenbrough™ Needle, which is commonly used to puncture the atrial septum of the heart. This device is a stiff elongated needle, which is structured such that it may be introduced into a body of the patient via the femoral vein and directed towards the heart. This device relies on the use of mechanical force to drive the sharp tip through the septum. Alternatively, radiofrequency perforation apparatuses have been developed, whereby the septal perforation is accomplished by the application of focused radiofrequency energy to the septal tissue via an electrode at the distal end of a relatively thin conductive probe.

Such perforation devices are often used in conjunction with a dilator to help support and guide the perforation device. Such dilators are often used in conjunction with a therapy sheath adapted to deliver a therapy to the patient.

SUMMARY

In Example 1, an enhanced dilator includes a dilator shaft defining a lumen for receiving a functional device (e.g., a puncturing device) therethrough. The dilator shaft includes a proximal portion for manipulation by a user and a distal portion to placement in or near the heart. A dilator hub is coupled to the proximal portion of the dilator shaft and includes a rotational coupling structure for coupling to a corresponding hub of a therapy sheath wherein the rotational coupling structure inhibits relative rotation between the dilator and the sheath Example 2 is the dilator of Example 1 wherein the sheath is a therapy sheath.

Example 3 is the dilator of Examples 1 or 2, wherein the puncturing device is an RF puncturing device or mechanical needle.

Example 4 is the dilator of any of Examples 1-3, wherein the rotational coupling structure includes a protrusion adapted to mate with a recess in the sheath hub.

Example 5 is the dilator of any of Examples 1-4, wherein the dilator hub includes an angled disengagement surface adapted to contact a mating surface on the sheath hub, wherein the mating surface is configured to generate an axial disengagement force upon the disengagement surface.

Example 6 is the dilator of Example 5, wherein the angled disengagement surface includes a first surface that is not parallel to a second surface associated with the mating surface.

Example 7 is the dilator of any of Examples 1-6, wherein the shaft includes a reinforcing member.

Example 8 is the dilator of any of Examples 1-7, wherein the distal portion includes one or more radiopaque marker.

Example 9 is the dilator of any of Examples 1-8, wherein the rotational coupling structure includes a first surface configured to contact a first surface of a recess located on the sheath hub.

Example 10 is the dilator of Example 8, wherein the rotational coupling structure includes a second surface configured to contact a second surface of the recess located on the sheath hub.

In Example 11, an enhanced dilator for coupling with a therapy sheath having a sheath hub. The enhanced dilator includes a dilator shaft defining a lumen for receiving a puncturing device therethrough. The dilator shaft is structured to provide support for the puncturing device when the puncturing device is used to create a puncture in a tissue. The dilator shaft includes a proximal portion and a distal portion and includes a dilator hub connected to the proximal. The dilator hub including a resilient coupling system for coupling to the sheath hub.

Example 12 is the dilator of Example 11, wherein the resilient coupling system includes a hexagonal distal end.

Example 13 is the dilator of Examples 11 or 12, wherein the dilator shaft includes a reinforcing member for supporting a flexible puncture device.

Example 14 is the dilator of any of Examples 11-13, wherein the distal portion includes a radiopaque marker.

Example 15 is the dilator of any of Examples 11-14, wherein the resilient coupling system includes a cylindrical body having an angled proximal end.

Example 16 is the dilator of any of Examples 11-15, wherein the resilient coupling system includes a plurality of circumferentially disposed protrusions.

In Example 17, a system includes a dilator including a shaft defining a lumen adapted for receiving and supporting a puncturing device. The shaft includes a proximal portion for manipulation by a user and a distal portion for placement in or near the heart for manipulation by a user. A dilator hub is coupled to the proximal portion of the dilator shaft. The dilator hub includes a rotational coupling structure. The system includes a sheath having a sheath body defining a lumen adapted for receiving the dilator. A sheath hub is coupled to a proximal portion of the sheath body. The sheath hub includes a recess for coupling with the rotational coupling structure to inhibit relative rotation between the dilator and the sheath.

Example 18 is the system of Example 17, wherein the rotational coupling structure includes one or more resilient member.

Example 19 is the system of Examples 17 or 18, wherein the recess includes a generally rectangular shape surrounding the lumen adapted for receiving the dilator.

Example 20 is the system of any of Examples 17-19, wherein the rotational coupling structure includes a first surface configured to contact a first inner portion of the recess and a second surface configured to contact a second inner portion of the recess.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1A:
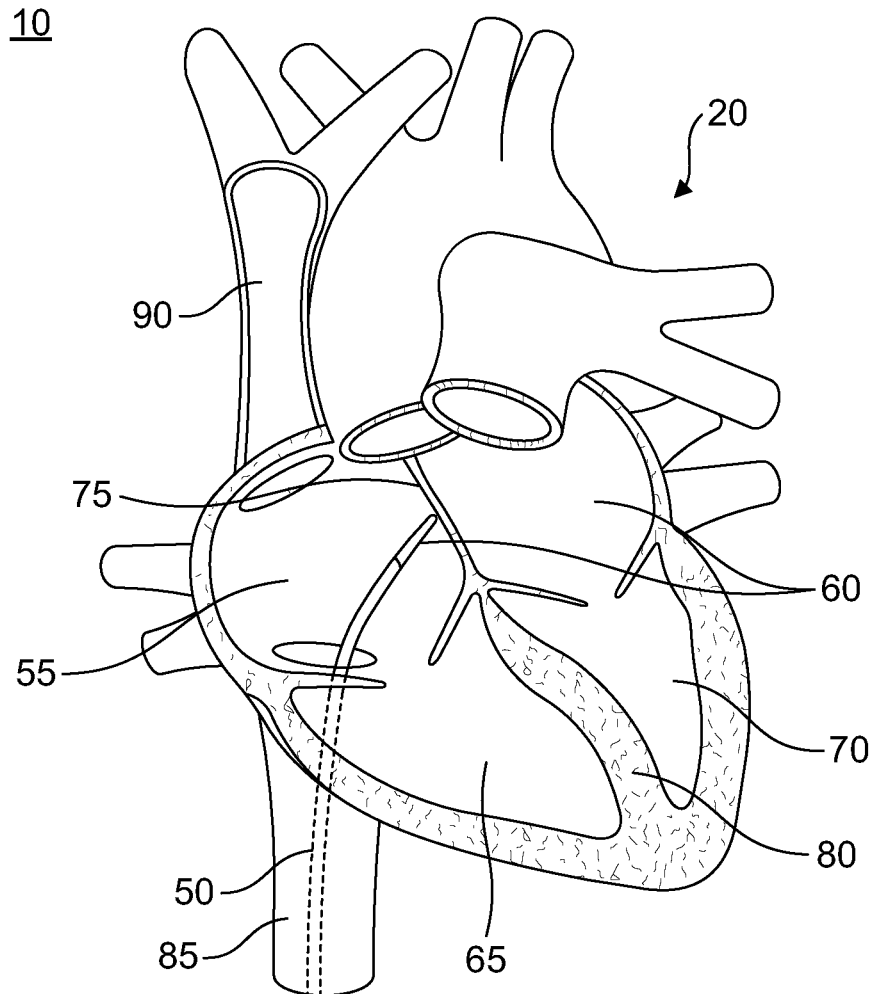
FIGS. 1A-1C are schematic illustrations of a medical procedure within a patient's heart utilizing a transseptal access system according to embodiments of the invention.

While the invention is amenable to various modifications and alternative forms, specific embodiments have been shown by way of example in the drawings and are described in detail below. The intention, however, is not to limit the invention to the embodiments described. On the contrary, the invention is intended to cover all modifications, equivalents, and alternatives falling within the scope of the invention as defined by the appended claims.

DETAILED DESCRIPTION

Figure 1B:
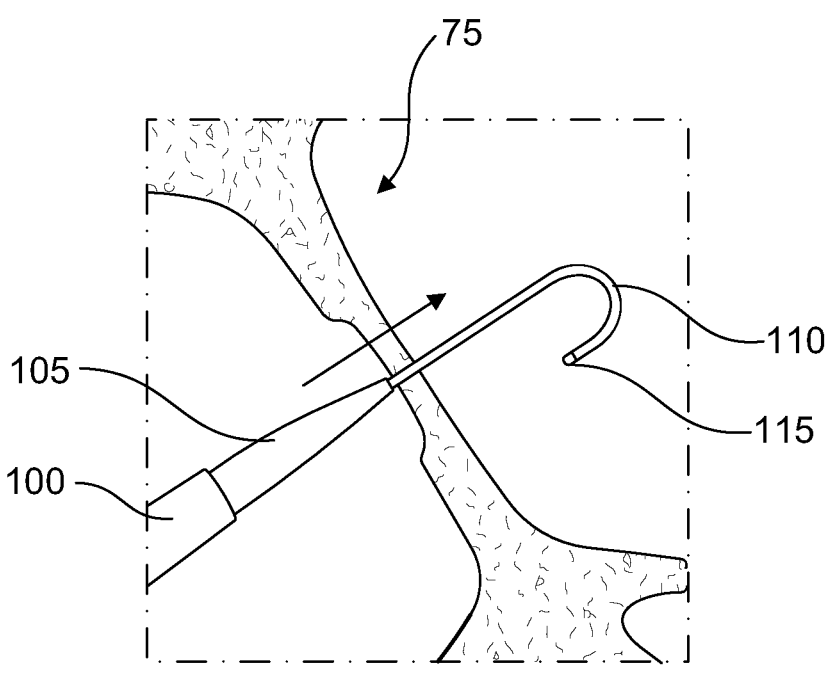
Figure 1C:
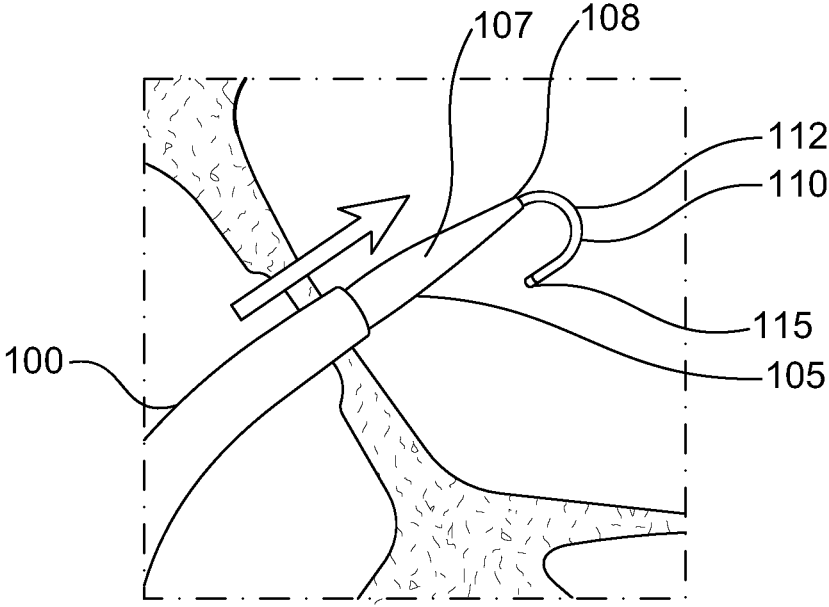

FIGS. 1A-1C are schematic illustrations of a medical procedure 10 within a patient's heart 20 utilizing a transseptal access system 50 according to embodiments of the disclosure. As is known, the human heart 20 has four chambers, a right atrium 55, a left atrium 60, a right ventricle 65 and a left ventricle 70. Separating the right atrium 55 and the left atrium 60 is an atrial septum 75 and separating the right ventricle 65 and the left ventricle 70 is a ventricular septum 80. As is further known, deoxygenated blood from the patient's body is returned to the right atrium 55 via an inferior vena cava (IVC) 85 or a superior vena cava (SVC) 90.

Various medical procedures have been developed for diagnosing or treating physiological ailments originating within the left atrium 60 and associated structures. Exemplary such procedures include, without limitation, deployment of diagnostic or mapping catheters within the left atrium 60 for use in generating electroanatomical maps or diagnostic images thereof. Other exemplary procedures include endocardial catheter-based ablation (e.g., radiofrequency ablation, pulsed field ablation, cryoablation, laser ablation, high frequency ultrasound ablation, and the like) of target sites within the chamber or adjacent vessels (e.g., the pulmonary veins and their ostia) to terminate cardiac arrythmias such as atrial fibrillation and atrial flutter. Still other exemplary procedures may include deployment of left atrial appendage (LAA) closure devices. Of course, the foregoing examples of procedures within the left atrium 60 are merely illustrative and in no way limiting with respect to the present disclosure.

The medical procedure 10 illustrated in FIGS. 1A-1C is an exemplary embodiment for providing access to the left atrium 60 using the transseptal access system 50 for subsequent deployment of the aforementioned diagnostic and/or therapeutic devices within the left atrium 60. As shown in FIGS. 1A-1C, target tissue site can be defined by tissue on the atrial septum 75. In the illustrated embodiment, the target site is accessed via the IVC 85, for example through the femoral vein, according to conventional catheterization techniques. In other embodiments, access to the target site on the atrial septum 75 may be accomplished using a superior approach wherein the transseptal access system 50 is advanced into the right atrium 55 via the SVC 90.

In the illustrated embodiment, the transseptal access system 50 includes an introducer sheath 100, a dilator 105 having a dilator body 107 and a tapered distal tip portion 108, and a perforation device (e.g., a radiofrequency (RF) perforation device) 110 having distal end portion 112 terminating in a tip electrode 115. As shown, in the assembled use state illustrated in FIGS. 1A-1C, the RF perforation device 110 can be disposed within the dilator 105, which itself can be disposed within the sheath 100. In one embodiment in which the transseptal access system 50 is deployed into the right atrium 55 via the IVC 105, a user introduces a guidewire (not shown) into a femoral vein, typically the right femoral vein, and advances it towards the heart 20. The sheath 100 may then be introduced into the femoral vein over the guidewire, and advanced towards the heart 20. In one embodiment, the distal ends of the guidewire and sheath 100 are then positioned in the SVC 90. These steps may be performed with the aid of an imaging system, e.g., fluoroscopy or ultrasonic imaging. The dilator 105 may then be introduced into the sheath 100 and over the guidewire, and advanced through the sheath 100 into the SVC 90. Alternatively, the dilator 105 may be fully inserted into the sheath 100 prior to entering the body, and both may be advanced simultaneously towards the heart 20. When the guidewire, sheath 100, and dilator 105 have been positioned in the SVC 90, the guidewire is removed from the body, and the sheath 100 and the dilator 105 are retracted so that their distal ends are positioned in the right atrium 55. The RF perforation device 110 described can then be introduced into the dilator 105, and advanced toward the heart 20.

Subsequently, the user may position the distal end of the dilator 105 against the atrial septum 75, which can be done under imaging guidance. The RF perforation device 110 is then positioned such that electrode 115 is aligned with or protruding slightly from the distal end of the dilator 105. The dilator 105 and the RF perforation device 110 may be dragged along the atrial septum 75 and positioned, for example against the fossa ovalis of the atrial septum 75 under imaging guidance. A variety of additional steps may be performed, such as measuring one or more properties of the target site, for example an electrogram or ECG (electrocardiogram) tracing and/or a pressure measurement, or delivering material to the target site, for example delivering a contrast agent. Such steps may facilitate the localization of the tip electrode 115 at the desired target site. In addition, tactile feedback provided by medical RF perforation device 110 is usable to facilitate positioning of the tip electrode 115 at the desired target site.

With the tip electrode 115 and dilator 105 positioned at the target site, energy is delivered from an energy source, e.g., an RF generator, through the RF perforation device 110 to the tip electrode 115 and the target site. In some embodiments, the energy is delivered at a power of at least about 5 W at a voltage of at least about 75 V (peak-to-peak), and functions to vaporize cells in the vicinity of the tip electrode 115, thereby creating a void or perforation through the tissue at the target site. The user then applies force to the RF perforation device 110 so as to advance the tip electrode 115 at least partially through the perforation. In these embodiments, when the tip electrode 115 has passed through the target tissue, that is, when it has reached the left atrium 60, energy delivery is stopped. In some embodiments, the step of delivering energy occurs over a period of between about 1 second and about 5 seconds.

With the tip electrode 115 of the RF perforation device 110 having crossed the atrial septum 75, the dilator 105 can be advanced forward, with the tapered distal tip portion 108 operating to gradually enlarge the perforation to permit advancement of the distal end of the sheath 100 into the left atrium 60.

In some embodiments, the distal end portion 112 of the RF perforation device 110 may be pre-formed to assume an atraumatic shape such as a J-shape (as shown in FIGS. 1B-1C), a pigtail shape or other shape selected to direct the tip electrode 115 away from the endocardial surfaces of the left atrium 60. Examples of such RF perforation devices can be found, for example, in U.S. patent application Ser. Nos. 16/445,790 and 16/346,404 assigned to Baylis Medical Company, Inc. The aforementioned pre-formed shapes can advantageously function to minimize the risk of unintended contact between the tip electrode 115 and tissue within the left atrium 60, and can also operate to anchor the distal end portion 112 within the left atrium 60 during subsequent procedural steps. For example, in embodiments, the RF perforation device 110 can be structurally configured to function as a delivery rail for deployment of a relatively larger bore therapy delivery sheath and associated dilator(s). In such embodiments, the dilator 105 and the sheath 100 are withdrawn following deployment of the distal end portion 112 of the RF perforation device 110 into the left atrium 60. The anchoring function of the pre-formed distal end portion 112 inhibits unintended retraction of the distal end portion 112, and corresponding loss of access to the perforated site on the atrial septum 75, during such withdrawal.

Various medical procedures have been developed for diagnosing or treating physiological ailments originating within the left atrium 60 and associated structures. Exemplary such procedures include, without limitation, deployment of diagnostic or mapping catheters within the left atrium 60 for use in generating electroanatomical maps or diagnostic images thereof. Other exemplary procedures include endocardial catheter-based ablation (e.g., radiofrequency ablation, pulsed field ablation, cryoablation, laser ablation, high frequency ultrasound ablation, and the like) of target sites within the chamber or adjacent vessels (e.g., the pulmonary veins and their ostia) to terminate cardiac arrythmias such as atrial fibrillation and atrial flutter. Still other exemplary procedures may include deployment of left atrial appendage (LAA) closure devices. Of course, the foregoing examples of procedures within the left atrium 60 are merely illustrative and in no way limiting with respect to the present disclosure.

In certain embodiments, catheters, therapy devices and sheaths can be deployed through the sheath 100, after it is successfully deployed into the desired heart chamber (e.g., the left atrium). In other embodiments, the therapy device (e.g., mapping catheter, therapy sheath, medical device, etc.) is part of the sheath 100, creating a therapy sheath.

Figure 2A:
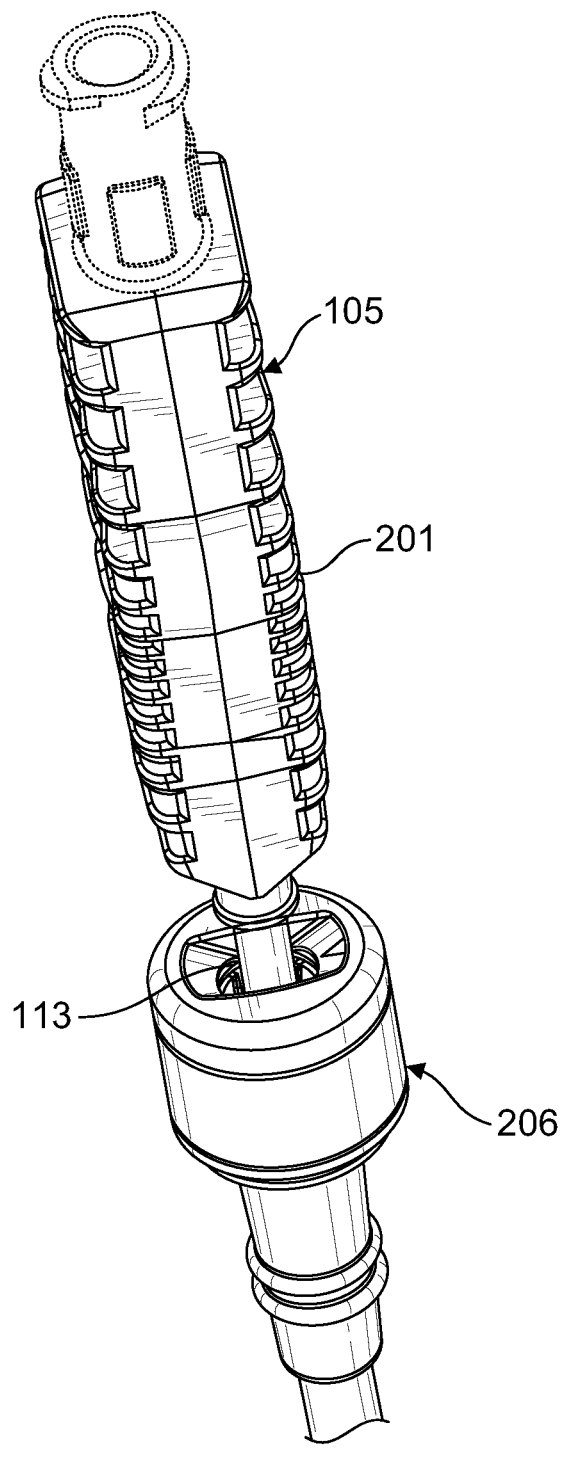
FIGS. 2A-2D are perspective views of a dilator and sheath according to embodiments of the invention.
Figure 2B:
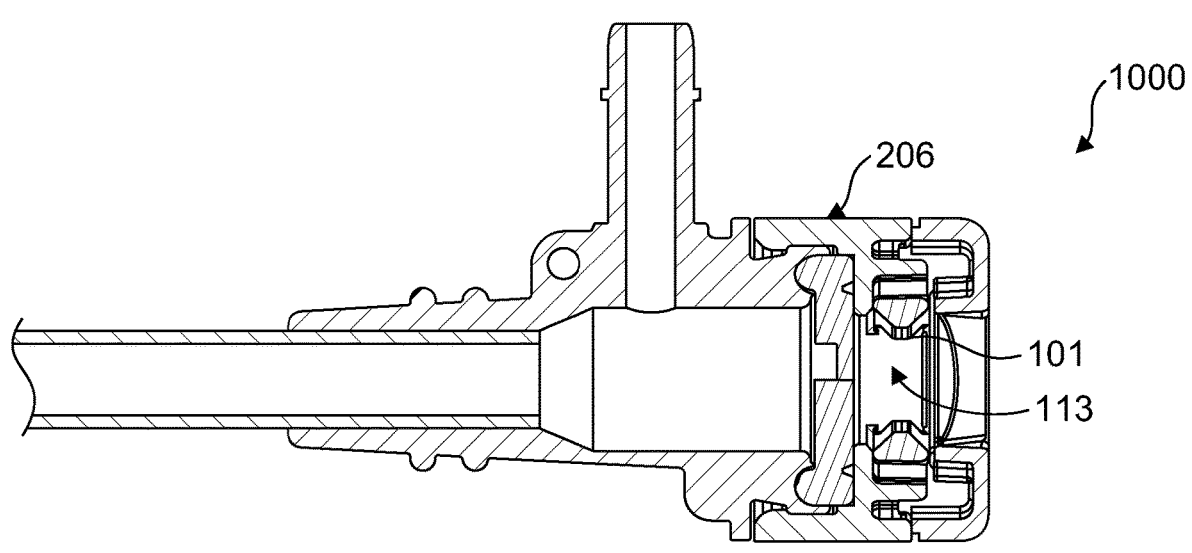
Figure 2C:
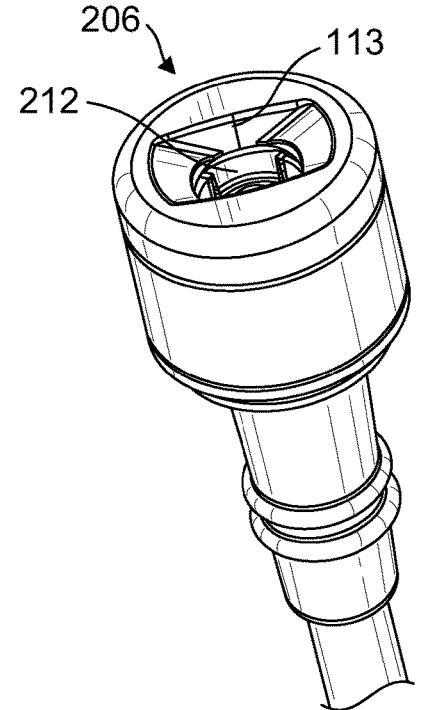
Figure 2D:
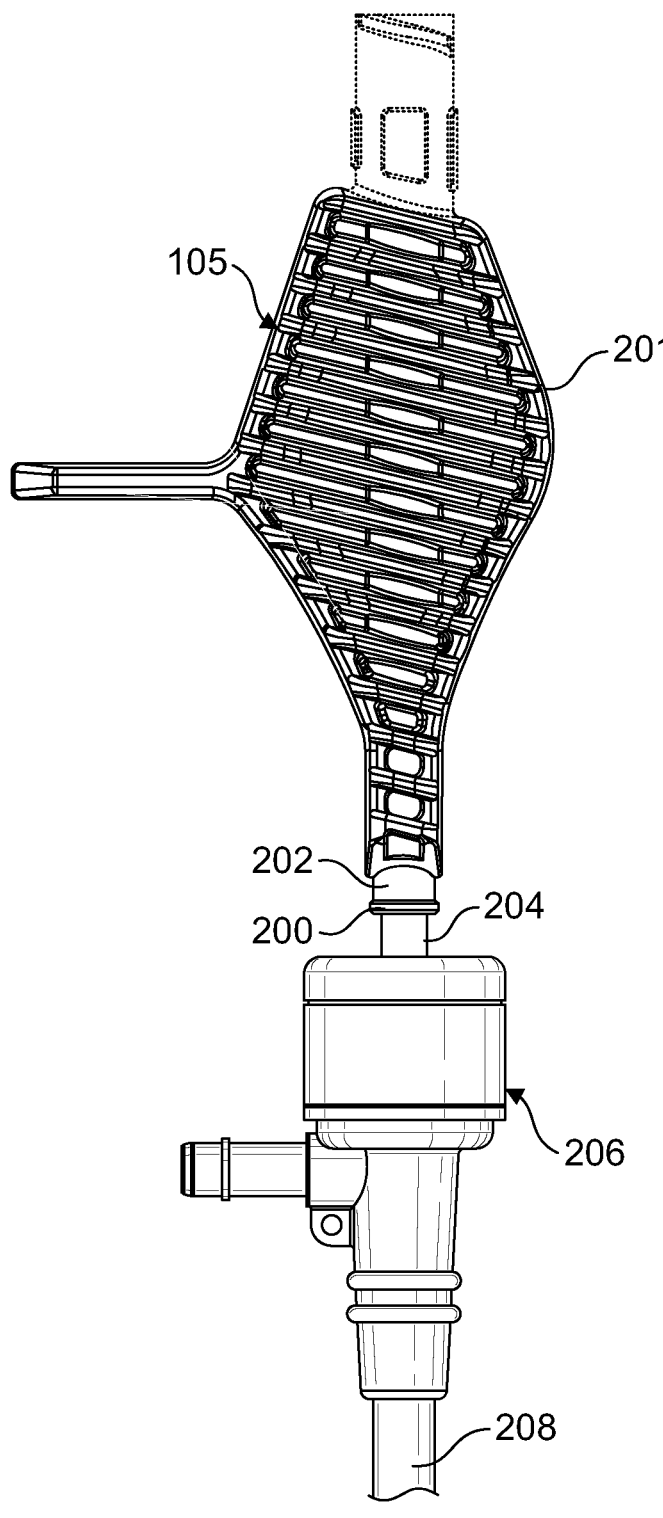

FIGS. 2A-2B are perspective views of a dilator and sheath according to some embodiments of the disclosure. As shown, the dilator 105 is partially inserted into a lumen of the sheath 100. The dilator 105 includes a handle 201, a dilator hub 202 and a dilator shaft 204. The sheath 100 includes a sheath hub 206 and a sheath body 208.

A releasable coupling mechanism 300 is configured for releasably coupling two corresponding members such as a first mating member 101 associated with the sheath hub 206 and a second mating member 200 associated with a dilator hub 202. Specifically, the releasable coupling system comprises a coupling mechanism 300 comprising coupling member 1000, a first mating member 101, and a second mating member 200 that is receivable by the first mating member 101 (for example through an opening 113) to be coupled to the first mating member 101 by the coupling member 1000. In conventional systems, the coupling member 1000 is configured for corresponding first and second mating members having designated materials and dimensions to couple to one another. In such cases, each of the first and second mating member is designed to accommodate the other member. For example, a conventional sheath hub is designed for a corresponding dilator hub and the dimensions and material selection are optimized for the corresponding dilator hub. Additionally, the dimensions and material selection of the dilator hub are optimized for the corresponding sheath hub.

Figure 3:
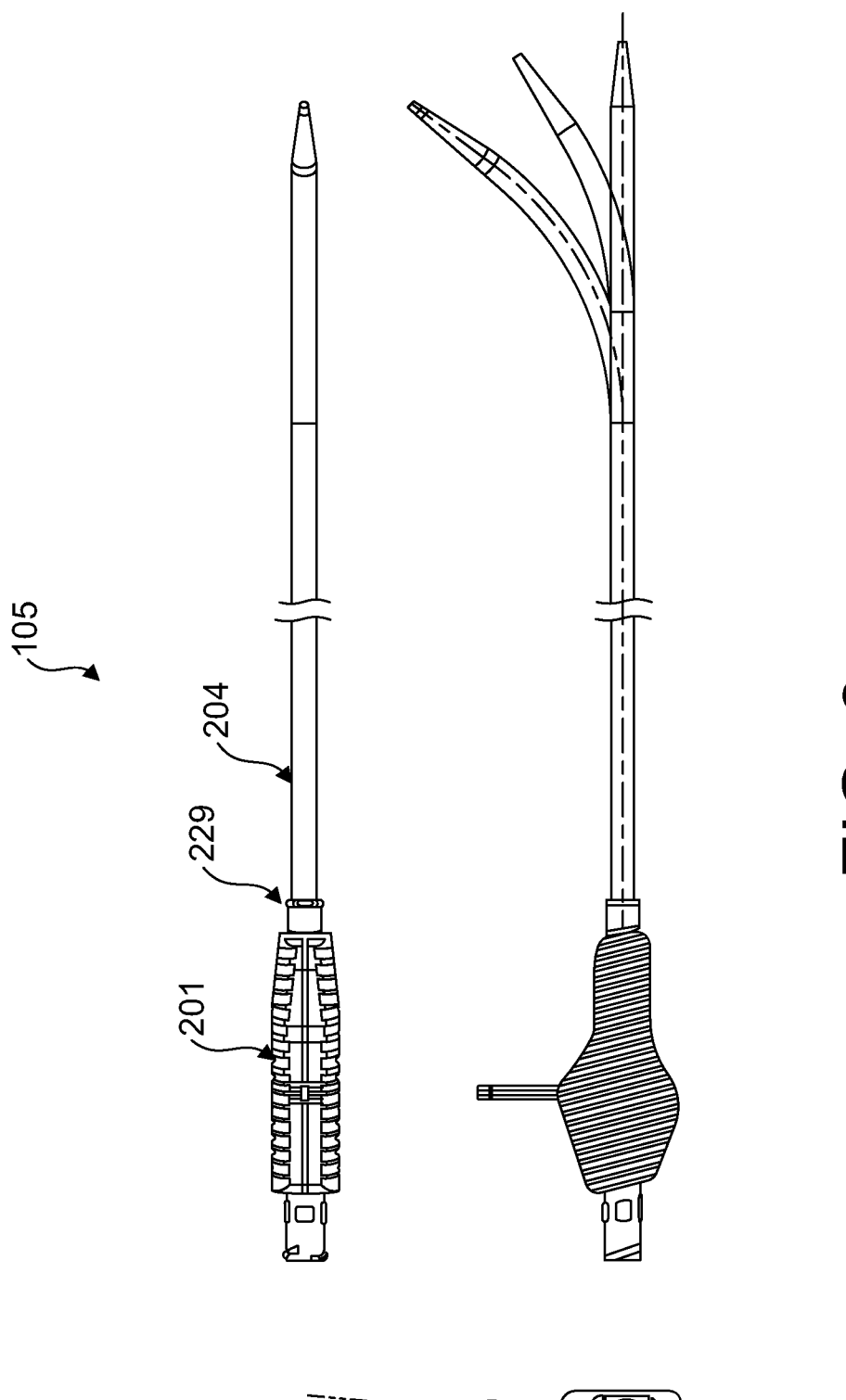
FIG. 3 is an illustration of an enhanced dilator in accordance with an embodiment of the present invention.

FIG. 3 shows an embodiment of the present invention of a dilator 105, also referred to as an enhanced dilator 105 configured to support a crossing device and configured to detachably couple to a sheath 100, such as a therapy sheath. The enhanced dilator 105 comprises a dilator hub 202 comprising a resilient coupling system 229.

Figure 4A:
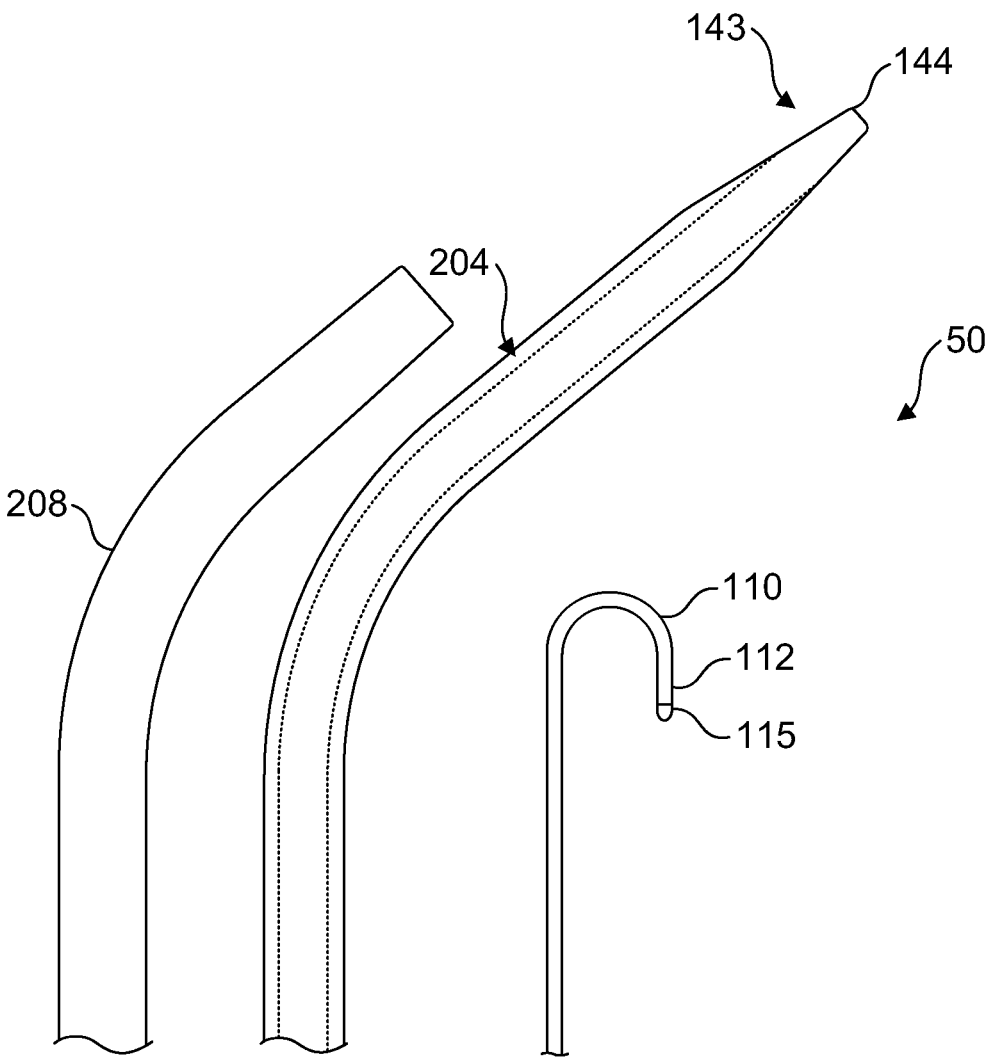
FIG. 4A and 4B are illustrations of transseptal assemblies comprising an enhanced dilator in accordance with an embodiment of the present invention.
Figure 4B:
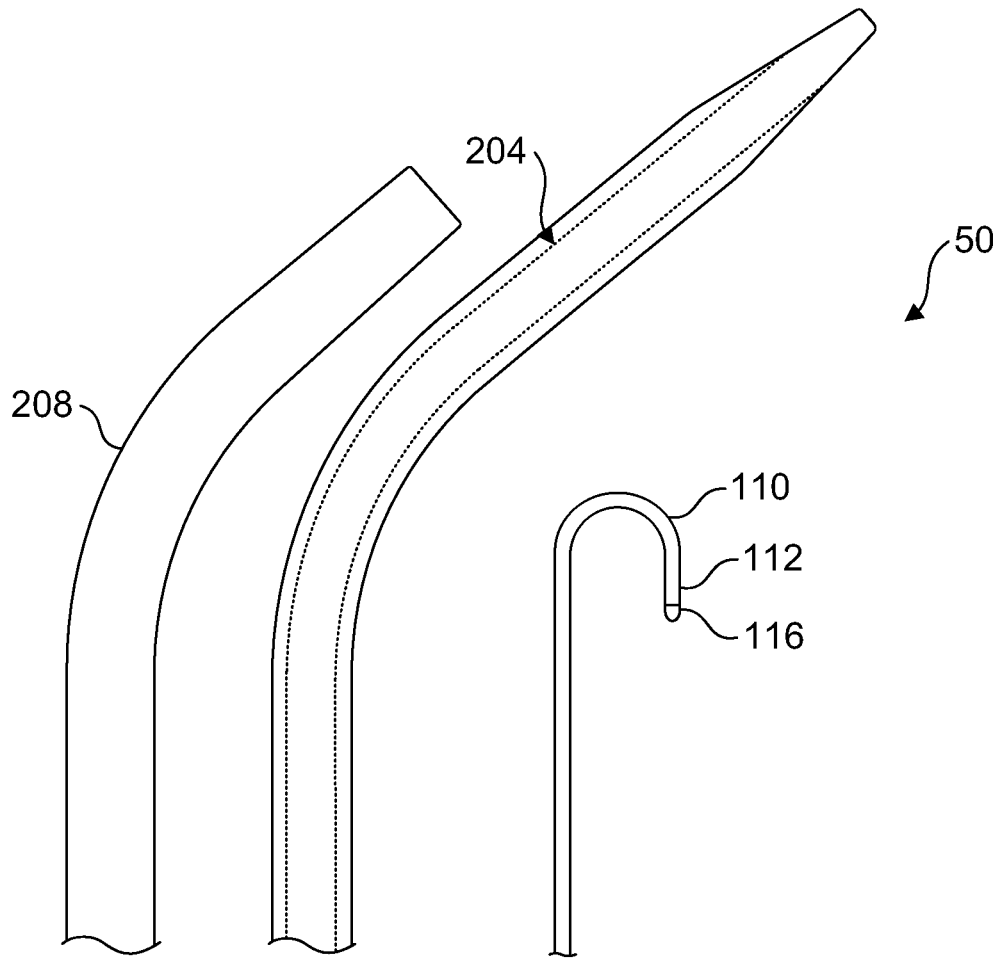

In some embodiments as shown in FIGS. 4A and 4B, the enhanced dilator 105 is configured to support a flexible puncturing or perforation device 110. In some embodiments the flexible puncturing or perforation device 110 is a radiofrequency (RF) wire having a distal electrode 115 (FIG. 4A). In some embodiments, the RF wire is a 0.035" wire. In some such examples, the RF wire comprises a J-tip wire or in alternate example the RF wire comprises a pigtail wire. In other embodiments, the flexible puncturing or perforation device 110 is a mechanical puncturing wire including a sharp distal tip 116 (FIG. 4B). Moreover, it should be understood that the distal end of the enhanced dilator 105 may include various tips and configurations without straying from the intended scope of the present invention.

Figure 4C:
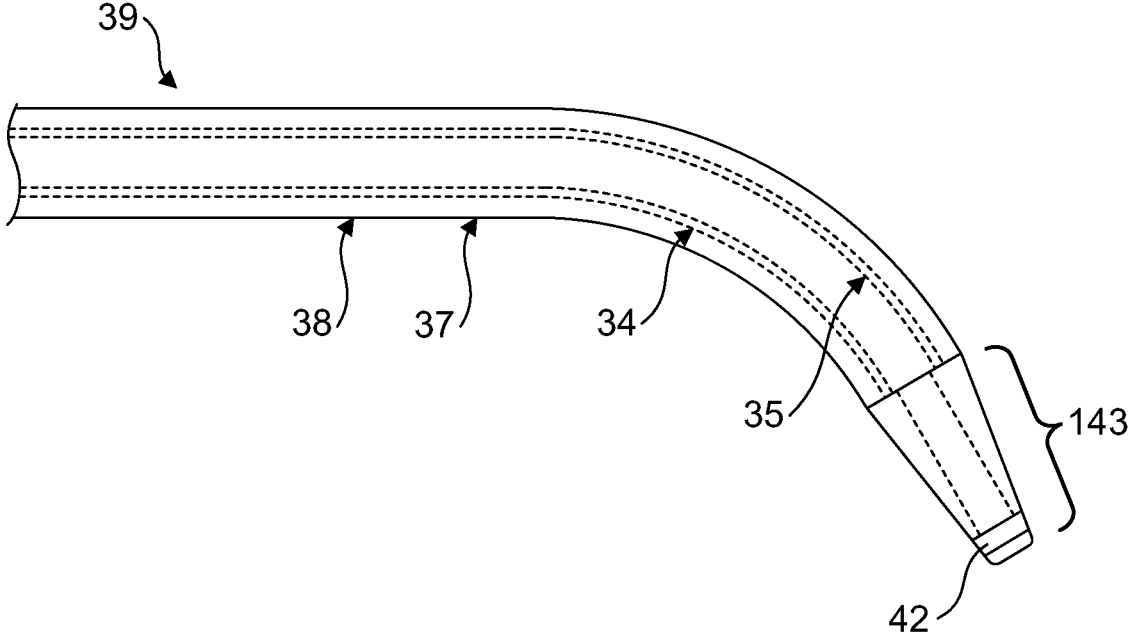
FIG. 4C is an illustration of an enhanced dilator in accordance with an embodiment of the present invention.

In embodiments where the enhanced dilator 105 is configured to support a flexible puncturing or perforation device 110, the enhanced dilator 105 comprises a reinforcing member 34, such as a stainless-steel hypo-tube, that extends longitudinally within one or more polymers layers. In one example, the reinforcing member 34, is positioned within polymer layers 35, 37 as shown in FIG. 4C. As such, the reinforcing member 34 defines the inner lumen of the dilator 105 In another example, the reinforcing member 34 is substantially surrounded by the one or more polymer layers 35, 37 such that the reinforcing member 34 is located between the inner polymer layer 35 and the outer polymer layer 37. In other words, the reinforcing member 34 (such as a stainless-steel hypotube) is sandwiched or located between two polymer layers. In some such examples, the inner and outer polymer layers 35, 37 comprise high density polyethylene (HDPE). In alternative embodiments, the outer layer 37 may be comprised of Pebax, low density polyethylene (LDPE), or medium density polyethylene (MDPE).

In some such embodiments, the enhanced dilator 105 provides sufficient stiffness to the puncturing device 110 such as the RF wire to enable sufficient force transmission to enable forces to be transmitted from the proximal end to the distal end of the assembly. As such, the enhanced dilator provides sufficient stiffness to the puncturing device to enable torque applied by the user to be transmitted to the distal end of the assembly.

In some such examples, the reinforcing member 34 provides sufficient stiffness to the enhanced dilator to enable sufficient force transmission to enable force to be transmitted from the proximal end to the distal end of the assembly 50. More specifically, the reinforcing member 34 provides sufficient stiffness to the assembly 50 such that the substantially flexible puncturing or perforation device 110 (such as an RF wire) together with the enhanced dilator 105 is capable of sufficient force transmission to enable forces applied by the user to be transmitted to a distal end of the assembly 50 (and thus allows force to be transmitted to a distal end of the substantially flexible puncturing or perforation device 110).

As such, the reinforcing member 34 is capable of imparting force transmission capabilities to the substantially flexible RF wire, which when used together with the enhanced dilator 105 is capable of force transmission to enable forces applied by the user to be transmitted to a distal end of the assembly 50, for example for engaging tissue at a target tissue site. As such, the reinforcing member 34 functions as a force transmitting portion of the assembly 50. Additionally, the reinforcing member 34 provides sufficient stiffness to enable torque to be transmitted to a distal end of the assembly 50. As such, the reinforcing member 34 provides sufficient stiffness to the assembly as a whole, wherein the substantially flexible puncturing or perforation device 110 together with the enhanced dilator 105 provides sufficient stiffness to the assembly 50 to enable torque applied by a user to be transmitted to a distal end of the assembly 50 (and thus allows torque to be transmitted to a distal end of the substantially flexible puncturing or perforation device 110).

In some embodiments of the present invention, the force transmitting portion of the assembly 50 has a force transmitting portion flexural rigidity of at least about 0.0085 $Nm^2$, for example about 0.0115 $Nm^2$. In some embodiments of the present invention, the force transmitting portion of the assembly is the enhanced dilator 105 that has a stiffness or rigidity with a flexural rigidity value of at least about 0.0115

$Nm^2$ to enable sufficient force transmission to enable force to be transmitted to a distal end of the assembly 50. In some such examples, the enhanced dilator 105 has a flexural rigidity of about 0.0085 $Nm^2$ to about 0.0145 $Nm^2$. In one such example, the enhanced dilator 105 has a flexural rigidity of at least about 0.0085 $Nm^2$, for example about 0.0115 $Nm^2$. In a specific example, the enhanced dilator 210 has a flexural rigidity about 0.0085 $Nm^2$ to about 0.0145 $Nm^2$. While such values provided herein exemplify the present varied embodiments of the present invention, flexural rigidity may vary in accordance with the given implementation of the invention. In some embodiments, the reinforcing member 34 is shapeable to enable the enhanced dilator 105 to be re-shaped to modify the curve to optimize the position of the assembly 50 against the target tissue site, such as the fossa of the septum of the heart.

In some embodiments, as shown in FIG. 3, the dilator hub 202 of the enhanced dilator 105 comprises a resilient coupling system 229. FIGS. 10A and 10B illustrate an embodiment of a resilient coupling system 229. The resilient coupling system 229 comprises a distal end 231. The outer surface of the distal end 231 engages with an internal surface of a sheath hub. In some embodiments, the distal end 231 couples to the sheath hub via a press fit. In alternate embodiments, the distal end 231 couples to the sheath hub via a snap fit.

Figure 7A:
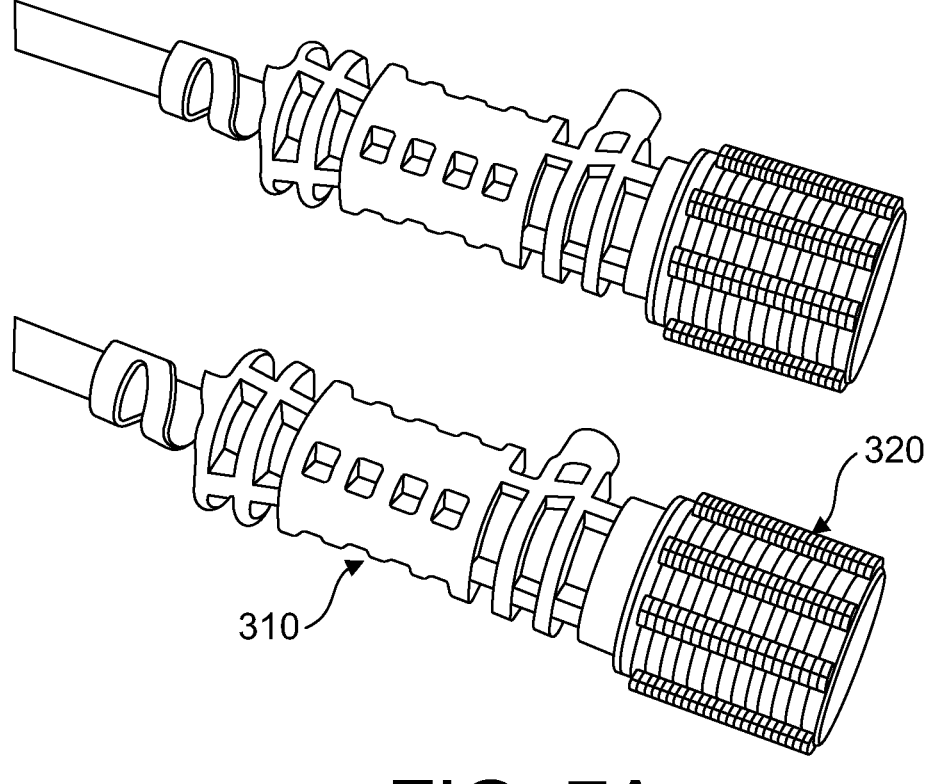
FIGS. 7A and 7B show a sheath hub and an enhanced dilator being inserted into the sheath hub, respectively, according to embodiment of the present invention.
Figure 7B:
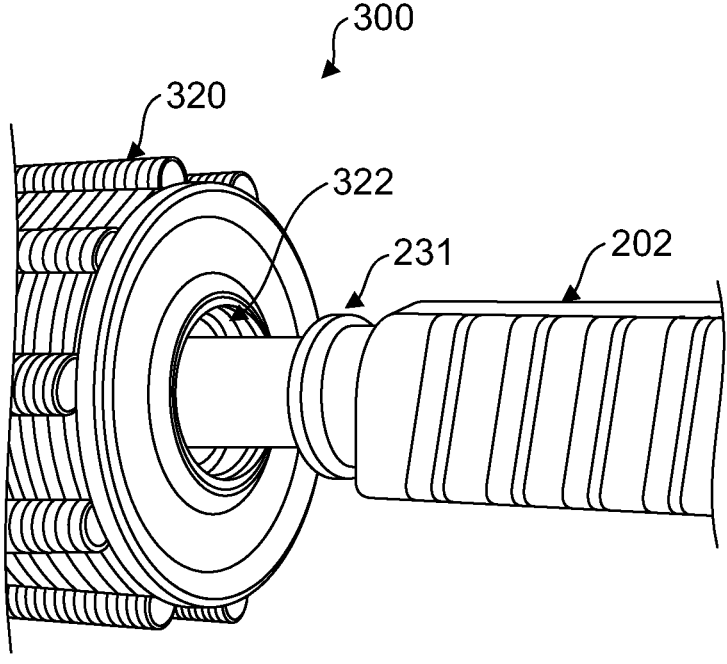

In some instances, the specification of the sheath hub is unknown. This may result from unpredictable variance in manufacturing processes or working with sheaths manufactured by a third party. In one example, a sheath 310 has a sheath hub 320 comprising a circular opening 322 for a corresponding circular dilator hub. FIGS. 7A and 7B show a therapy sheath 310 having a sheath hub 320 with a circular opening 322. However, the circular sheath hub 320 and its corresponding circular dilator hub require small tolerances to ensure that when the sheath and dilator are paired the dilator hub is not too large to fit with the sheath hub, or the dilator hub is not too small resulting in insufficient retention force of the dilator hub within the sheath hub.

Figures 6A, 6B, 6C:
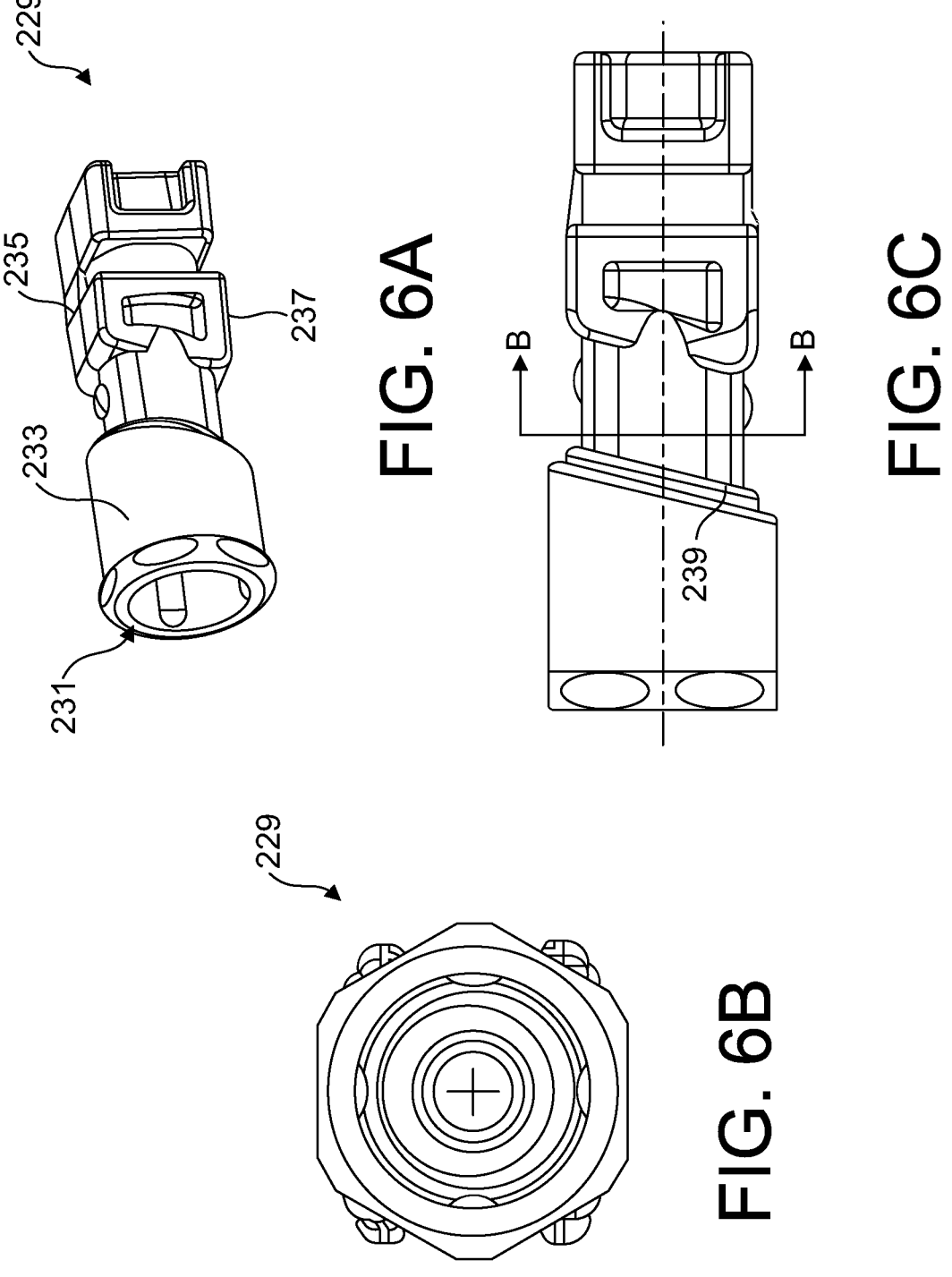
FIGS. 6A-6C are illustrations of a resilient coupling system in accordance with an embodiment of the present invention.

In such instances, an enhanced dilator 105 including a hub 202 comprising a resilient coupling system 229 may be used to accommodate a greater tolerance or variability of the sheath hub. In the embodiment of FIGS. 6A-6C, the distal end 231 includes a hexagonal shape and is configured to couple to a circular sheath hub 320. The hub 202 includes a cylindrical body 233 extending proximally of the distal end 231 and includes an angled proximal end 239. The hub 202 additionally includes a first surface 235 and a second surface 237 opposite the first surface 235. The distal end 231 is made of a resilient material such as thermoplastic. In some embodiments the resilient material is acrylonitrile butadiene styrene (ABS). In alternate embodiments, the resilient material is polycarbonate, high density polyethylene (HDPE), Nylon Styrene, Polypropylene, Acetal, or Polyethylene terephthalate glycol (PETG). In such embodiments, the outer diameter of the hexagon of the hexagonal distal end 231 corresponds with the larger opening of the sheath hub's tolerance as shown in FIG. 8.

Figure 8:
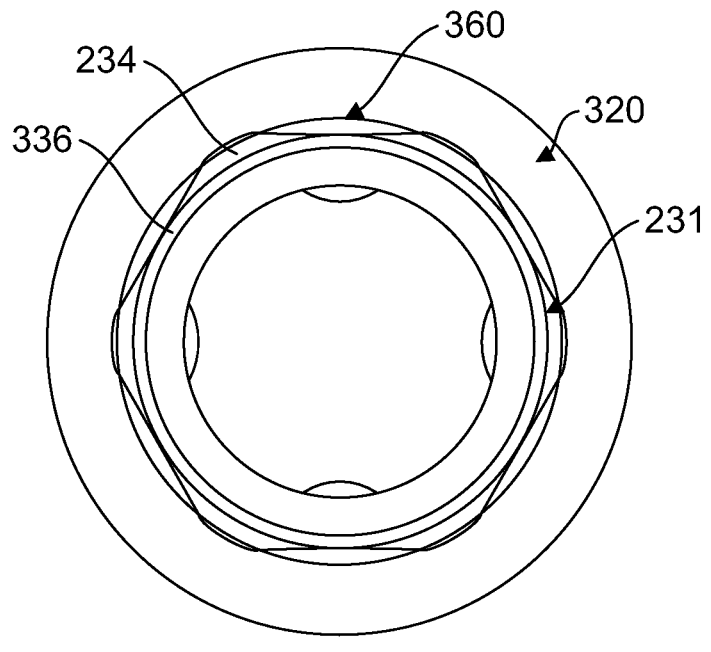
FIG. 8 is an illustration of a resilient coupling system positioned within a sheath hub in accordance with an embodiment of the present invention.

In the embodiment of FIG. 8 the hexagonal distal end 231 comprises rounded edges 234 for contacting the inner surface of the sheath hub and flat portions 336 creating gaps 360. The gaps 360 formed by the hexagonal flats 336 allow space into which material may deflect. In instances where the sheath hub was manufactured with a smaller opening, the hexagonal distal end 231 made of a resilient material may flex to accommodate the smaller opening. This is achieved by the resilient hexagon utilizing the gaps 360 as the resilient distal end 231 flexes into the gaps 360 allowing the hexagonal distal end 231 with a greater outer diameter fit into a smaller circular sheath hub. In an alternate embodiment, the sheath hub comprises a hexagonal opening and the resilient coupling system of the dilator hub comprises a resilient circular distal end. In this embodiment, the gaps are formed from the flat portions of the sheath hub opening. Similarly, in instances where the sheath hub was manufactured with a smaller opening, the resilient circular distal end may flex to into the gaps to accommodate the smaller opening.

Figure 9:
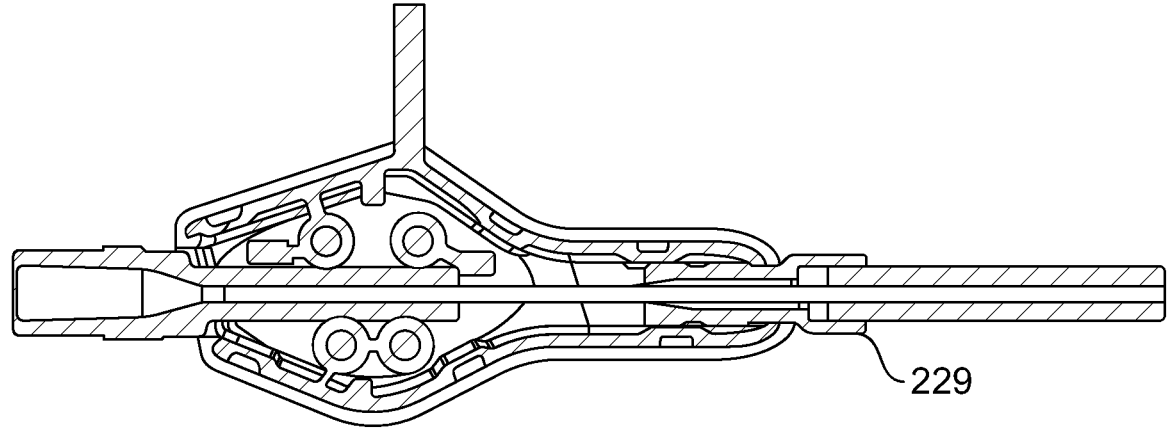
FIG. 9 is an illustration of a dilator hub of an enhanced dilator in accordance with an embodiment of the present invention.

In certain embodiments, the hexagonal distal end 231 of FIG. 10B comprises an outer diameter of about 6.5 mm. The resilient coupling system 229 of FIG. 6B is compatible with a sheath hub with a circular hub with a diameter of about 6.471 mm. In one embodiment, the distal end 231 is press fit into the circular sheath hub. In an alternate embodiment, the distal end 231 may snap fit into the sheath hub. In some embodiments, the dilator hub 202 comprises a clam shell wherein the resilient coupling system 229 is positioned at the distal end of the clam shell as illustrated in FIG. 9.

In one embodiment, as shown in FIG. 7A, the sheath 310 is a therapy sheath which is part of a therapeutic assembly that is not configured to support a flexible puncturing device. In this example, the enhanced dilator 105 may be used to support the flexible puncturing or perforation device 110 while being compatible to couple to the therapy sheath 310 via the resilient coupling assembly 229. The workflow of using the enhanced dilator 105 to support the flexible puncturing or perforation device 110 and therapy sheath 310 is described below. FIG. 7B illustrated a dilator hub 202 comprising a hexagonal distal end 231 being inserted into a sheath hub 320 having a circular opening 322.

Figures 5A, 5B, 5C:
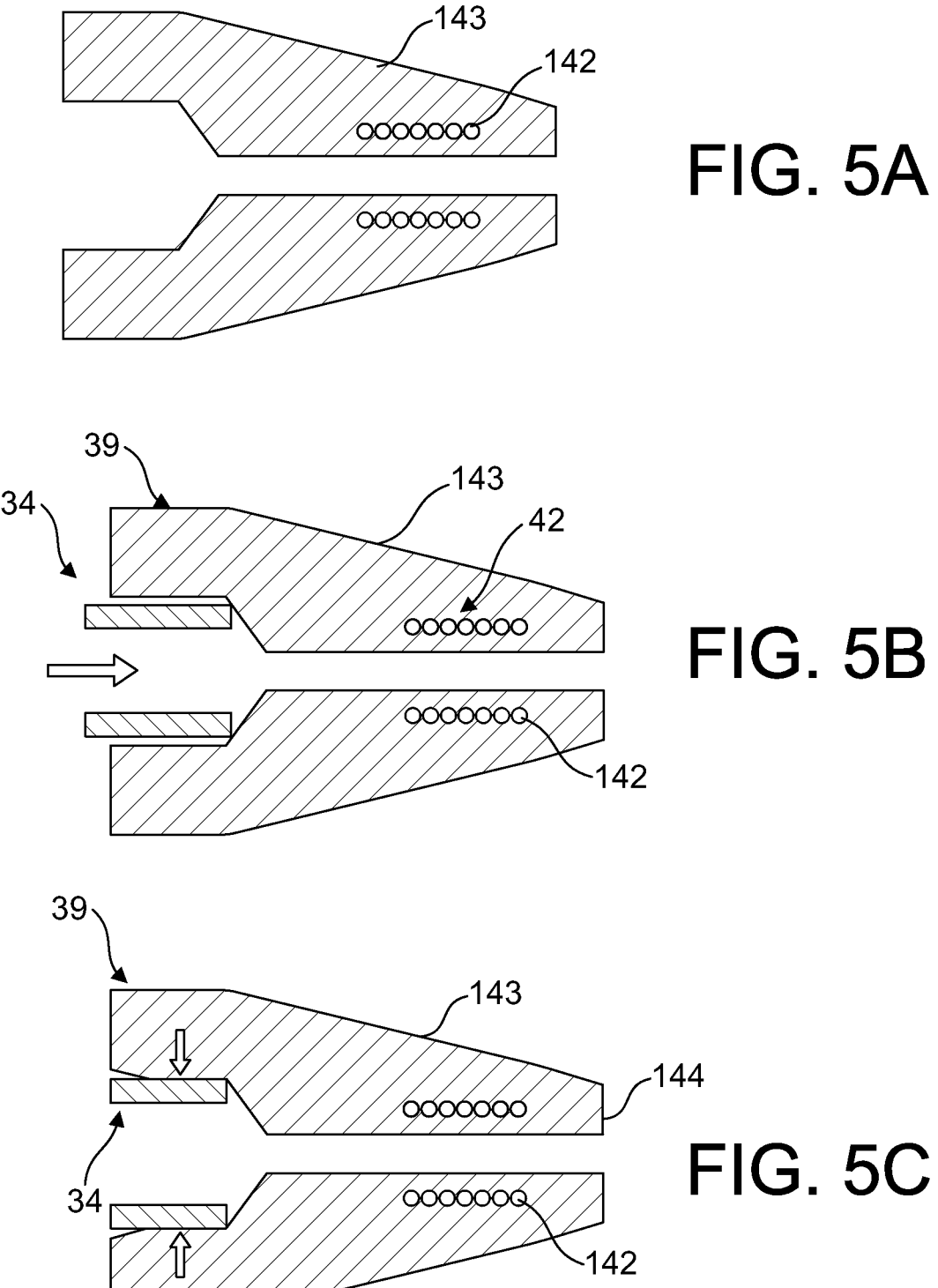
FIGS. 5A-5C illustrate an enhanced dilator, in accordance with additional alternate embodiments of the present invention.

In some embodiments, the enhanced dilator 105 comprises one or more radiopaque markers. In a specific example, as shown in FIG. 5A, 5B and 5C, the radiopaque marker 42 comprises a radiopaque coil 142 embedded within the polymer of the enhanced dilator 105 such as within the one or more polymer layers 38 (forming the polymer shaft 39), for example, at a distal tip thereof. In a more specific example, the radiopaque coil 142 is embedded within the one or more polymer layers such that the one or more polymer layers extend distally beyond the radiopaque coil 142. In some embodiments, the coil 142 is echogenic and can be visualized using ultrasonic imaging. In some embodiments, for example those shown in FIGS. 4C and 4D, the radiopaque marker 42 may take the form of a ring located near the distal tip 143 of the dilator 105.

In some embodiments of the present invention, a substantially flexible puncturing or perforation device 110 is provided (such as an RF guidewire) that comprises one or more device side radiopaque markers (or in other words one or more device radiopaque markers) at a distal end of thereof. In some such embodiments, as noted above, the enhanced dilator 105 also comprises a radiopaque marker at the distal end (as shown in FIGS. 5A-5C). In some such embodiments, the one or more device radiopaque markers are configured to co-operate with the enhanced dilator radiopaque marker 42 to indicate the relative position of the substantially flexible puncturing or perforation device 110 (such as an RF guidewire).

In some embodiments, the reinforcing member 34 such as a metal shaft or hypotube is also radiopaque. Additionally, in some such embodiments, polymers forming the enhanced dilator 105 may comprise polymer radiopaque filler such as barium sulfate 20% so there is contrast with the one or more markers 42 at the distal tip. In other words, this may allow the user to see the enhanced dilator 105 in comparison to the flexible puncturing or perforation device 110 under imaging, to see whether the flexible puncturing or perforation device 110 is positioned in or outside the enhanced dilator 105 [i.e., whether the distal segment of the flexible puncturing or perforation device 110 is distal to the enhanced dilator 105. In alternate embodiments, the enhanced dilator 105 comprises an echogenic coil at the distal end that may be visualized using ultrasonic imaging.

In some embodiments of the present invention, the enhanced dilator 105 comprises a substantially blunt distal tip or edge 144, as shown in FIG. 4A, to provide a substantially atraumatic distal tip 143, while providing the advantages of a substantially rigid or stiff enhanced dilator 105 (such as by providing the reinforcing member 34) therein. In some such embodiments, as noted above, an enhanced dilator 105 is provided, with reference again to FIG. 4A. The enhanced dilator 105 in some instances comprises a substantially blunt distal tip or edge 144 to provide a substantially atraumatic distal tip 144. In some such embodiments, the enhanced dilator 105 comprises a substantially thick distal wall along the distal tip 144 where the distal tip 144 is defined by a substantially rounded distal tip edge. In some such embodiments, the enhanced dilator 105 provides advantages of a dilator by providing a substantially atraumatic distal tip and additionally a tapered profile at the distal tip to provide ease of trackability and crossing while providing advantages associated with providing a substantially rigid body by providing a substantially rigid component (such as a reinforcing member 34 therein) in addition to enabling use of a flexible puncture or perforation device 110 for one or more of positioning, tracking devices, puncturing and anchoring. As previously described, the present invention of an enhanced dilator provides support for a puncturing device and is compatible with a therapy sheath.

This improves the efficiency of a procedure by eliminating steps from the workflow in procedures which may require specialty therapeutic devices, such as specialty therapy sheaths, to be used to deliver the end therapy devices once gaining access to the left atrium. Some examples of procedures requiring specialty therapy devices are cryoablations, left atrial appendage occlusions (LAAO), transcatheter aortic valve replacement (TAVR), transcatheter mitral valve repairs, transcatheter mitral valve replacements, pulse field ablations, and RF ablations. These procedures commonly require the use of end-therapy devices which can only be delivered with sheaths having inner diameters greater than the sheaths used during transseptal puncture. This is because such end-therapy devices are larger in size than transseptal puncture devices, such as mechanical needles, RF needles, and RF guidewires. Specifically, conventional transseptal puncture sheaths range from 8 to 13 French. Many sheaths are about 12.5 French in diameter, while some specialty sheaths, such as those used for cryoablation and LAAO, are sized 11.5 French or larger. Due to the difference in the size of the sheaths for end-therapy devices and transseptal puncture devices, multiple exchanges are typically required to both perform the transseptal procedure (i.e., the procedure for puncturing the septum) and deliver the end-therapy device to the left atrium.

Figure 10:
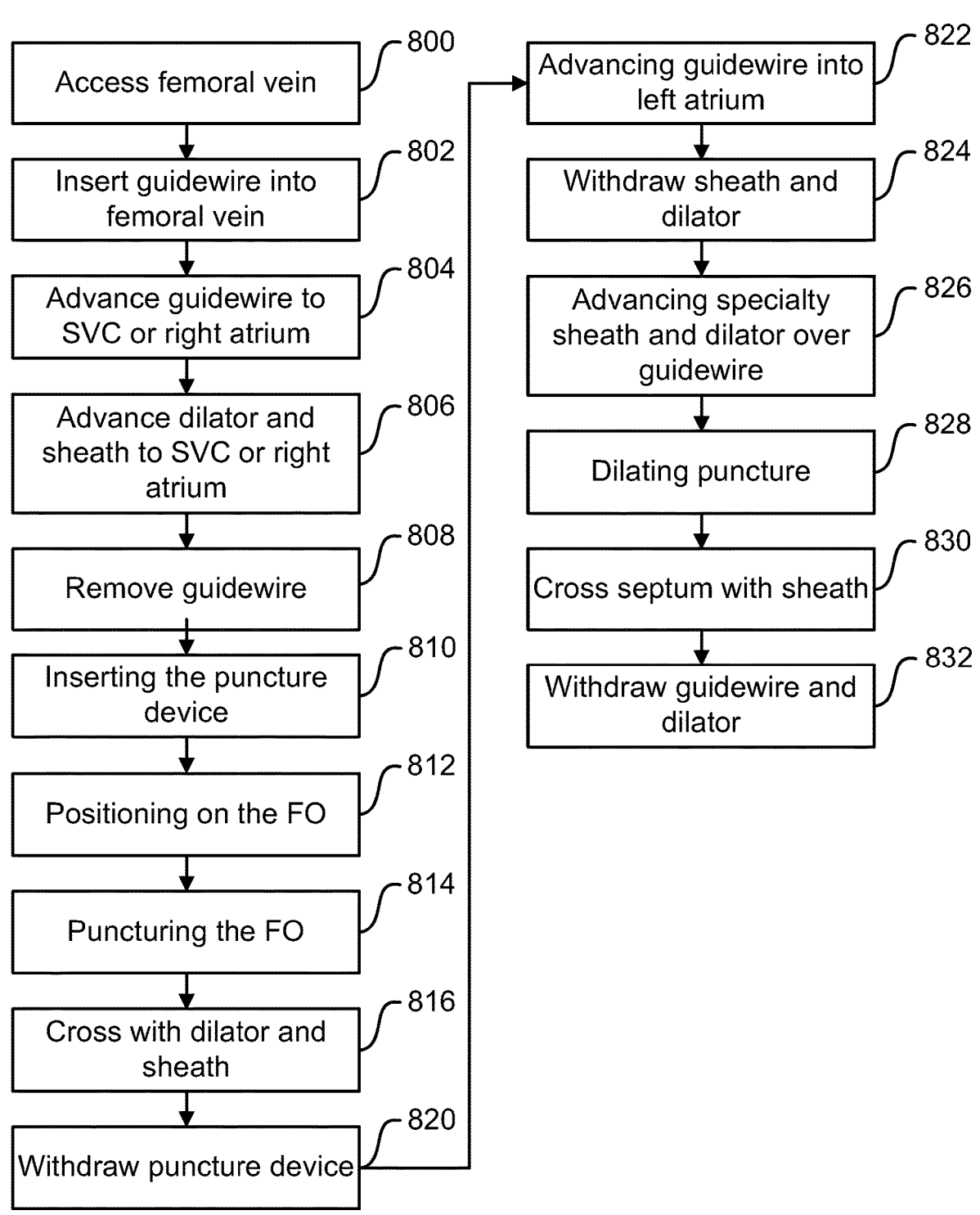
FIG. 10 illustrates a method of performing an end-therapy procedure in the left atrium of a patient.

One example of a current conventional workflow for these procedures is illustrated in FIG. 10. As a general overview, this method comprises the following steps: (i) Gaining percutaneous venous access, for example into the femoral vein, using traditional access procedures such as the Seldinger technique 800. (ii) Inserting a guidewire into the femoral vein 802. (iii) Advancing the guidewire to the superior vena cava (SVC) or right atrium 804. The guidewire anchors in the SVC or right atrium, and acts as a guiderail for advancing the other devices. (iv) Advancing a dilator and sheath into the SVC or right atrium, overtop of the guidewire 806. (v) Removing the guidewire 808; the sheath and dilator now act to form a channel which the puncturing device can be advanced through. (vi) Inserting and advancing the puncturing device through the sheath and dilator assembly 810. The distal tip of the puncturing device remains within the lumen of the dilator while (vii) position-ing the assembly on a target location on the fossa ovalis (FO) 812. The puncture site may be determined using various visualization methods such as fluoroscopy, electro-anatomi-cal mapping, or echogenic markers. Tenting the FO using the distal tip of the dilator and advancing the puncturing device, such that the distal tip of the puncturing device is contacting the FO, and (viii) puncturing the FO 814 and advancing the puncture device such that the distal tip is located in the left atrium. Upon completing the puncture, the physician may confirm access into the left atrium through various methods such as fluoroscopy, electro-anatomical mapping, pressure differentials, contrast injection, or echogenic markers. (xi) Advancing the dilator, enlarging the transseptal puncture, across the septum and crossing the septum with the sheath 816. (x) Withdrawing the puncturing device 820, followed by inserting and (xi) advancing the guidewire into the left atrium 822. (xii) Withdrawing the sheath and dilator 824, leaving the guidewire to act as a guiderail to advance the specialty devices into the left atrium. (xiii) Advancing the specialty sheath and dilator 826 over the guidewire. (xiv) Widening the puncture with the specialty dilator to allow for advancement of the specialty sheath 828. (xv) Crossing the septum, through the enlarged puncture, with the specialty sheath 830. (xvi) Withdrawing the guidewire and specialty dilator and inserting the end-therapy device 832 to complete the procedure.

Using the devices of the present invention, steps of the current conventional procedure may be eliminated, such as the steps of removing the guidewire (step (v), 808), inserting a puncture device (step (vi), 810), withdrawing the punc-turing device (step (x), 820), and inserting the guidewire (step (xi), 822). As the RF guidewire has characteristics of a guidewire and acts as the puncturing device, the present invention avoids the need for an additional puncturing device and, upon completing the puncture, the RF guidewire can simply be advanced into the left atrium, without needing to be exchanged.

Another advantage is that the stiffness and exchange length of the RF guidewire provides the support needed allow the use of larger, specialty sheaths when performing the transseptal puncture. An enhanced dilator, which has an inner diameter that accommodates the RF guidewire and an outer diameter that is near in size to the inner diameter of the larger specialty sheath, may be used in conjunction with the larger sheath. In other words, the dilator is dimensioned to fill the gap between the RF guidewire and the sheath. As a result, physicians may avoid the step of withdrawing the transseptal sheath and dilator (step (xii), 824) and instead are able to use the larger specialty therapy sheath with an enhanced dilator to perform both the puncture and to deliver the end-therapy devices.

Figure 11:
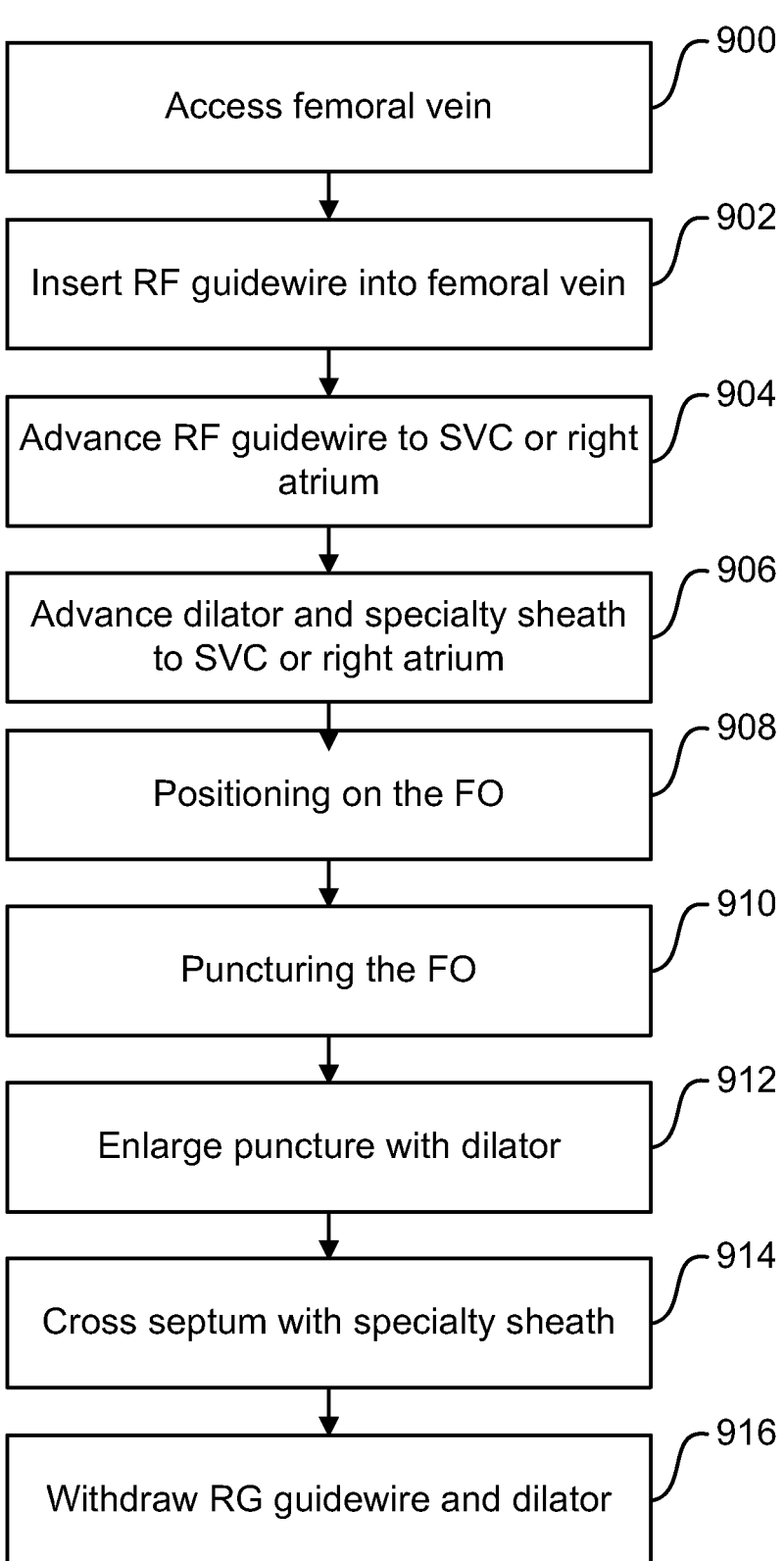
FIG. 11 illustrates a method with an improved workflow when performing an end-therapy procedure in the left atrium of a patient.

An example of the improved workflow, with use of the present invention, is illustrated in FIG. 11. This method comprises the steps of: (i) Gaining percutaneous venous access, for example into the femoral vein, using traditional access procedures such as the Seldinger technique 900. (ii) Inserting a flexible puncturing device into the femoral vein

902. (iii) Advancing the flexible puncturing device to the SVC or right atrium 904. The flexible puncturing device anchors in the SVC or right atrium, and acts as a guiderail for advancing the other devices. (iv) Advancing a specialty therapy sheath and enhanced dilator, which accommodates the larger outer diameter of the therapy sheath and supports the flexible puncturing device, into the SVC or right atrium, overtop of the flexible puncturing device 906. Retracting the distal tip of the flexible puncturing device such that it is positioned within the lumen of the dilator while (v) posi-tioning the assembly on a target location on the FO 908. The puncture site may be determined using various visualization methods such as fluoroscopy, electro-anatomical mapping, or echogenic markers. Tenting the FO using the distal tip of the enhanced dilator and advancing the flexible puncturing device, such that the distal tip of the RF guidewire is contacting the FO, and (vi) puncturing the FO 910 (for example, when then flexible puncturing device is an RF wire by energizing the RF wire) and advancing the flexible puncturing device through the septum such that the distal tip is in the left atrium. Upon completing the puncture, the physician may confirm access into the left atrium through various methods such as fluoroscopy, electro-anatomical mapping, pressure differentials, contrast injection, or echo-genic markers. (vii) Advancing the enhanced dilator across the septum 912, enlarging the puncture. (viii) Crossing the septum, through the enlarged puncture, with the specialty therapy sheath 914. (ix) Withdrawing the flexible puncturing device and enhanced dilator and inserting the end-therapy device 916 to complete the procedure. Thus, the number of steps were reduced (i.e., from 16 steps to nine steps); eliminating the steps of removing the guidewire (step (v), 808), inserting a puncture device (step (vi), 810), withdraw-ing the puncturing device (step (x), 820), re-inserting the guidewire (step (xi), 822), and withdrawing the transseptal sheath and dilator (step (xii), 824). The number of exchanges were reduced (i.e., from three exchanges to no exchanges), as there is no longer a need to exchange the initial guidewire for a puncturing device prior to puncturing the septum, the puncturing device for a guidewire after the puncture has been completed, and there is no exchange of the transseptal sheath and dilator for the specialty sheath and dilator. Lastly, the number of devices were reduced (i.e., from six devices to three devices); in the improved workflow, there is no separate guidewire and puncturing device, nor is there a need for a separate transseptal sheath and dilator and spe-cialty sheath and dilator.

Reducing the number of exchanges needed in this way provides numerous benefits and advantages when perform-ing these procedures. First, the proposed method does not require any exchanges, physicians avoid the potential loss of positioning throughout the procedure. Additionally, crossing the septum is more efficient as physicians are not required to use a smaller sheath and dilator to dilate the transseptal puncture prior to the passage of the larger sheath and dilator; this also avoids potential difficulties when crossing the atrial septum. Furthermore, the reduction in exchanges provides a clinical benefit as the number of exchanges performed during a procedure is associated with an increased risk of embolisms. In addition, in general fewer steps or exchanges also results in reduced procedure times.

In some embodiments, a mechanical puncturing guidewire or power wire may be used instead of an RF guidewire. In an alternative embodiment, a steerable needle may perform the puncture, however it would not provide the advantages of being used as a guidewire. Once the puncture is complete, the steerable needle would need to be removed and exchanged for a guidewire. In some embodiments of the present invention, the specialty therapy sheath may be a fixed curved sheath, while in other embodiments, it may be a uni- or multi-directional steerable sheath. Alternatively, in some embodiments, multiple telescoping sheaths may be used to improve target site-selection.

The dilator may be an enhanced dilator 105 to provide the physician with the ability to re-shape the dilator during the procedure, optimizing the positioning of the distal tip on the FO. The reinforced dilator 105 may include a radiopaque marker 42 located at the distal tip. This radiopaque marker 42 may be in the form of a radiopaque band or coil embedded within one of the polymer layers. The radiopaque marker 42 enables physicians to visualize the distal tip of the enhanced dilator 105 throughout the procedure. The shaft of the enhanced dilator 105 is dimensioned to accommodate flexible puncturing device and specialty therapy sheath. Specifically, the inner diameter of the enhanced dilator 105 corresponds to the outer diameter of the RF guidewire and the outer diameter of the enhanced dilator 105 corresponds to the inner diameter of the specialty therapy sheath. In some embodiments, the inner diameter of the shaft may range from 0.035" to 0.050", and in some embodiments, the inner diameter in the range of 0.038" to 0.044". The outer diameter of the shaft should be sized to accommodate the specialty sheath, for example, in some procedures the outer diameter of the shaft may be 0.151" (11.5 Fr) or larger. The wall thickness of the enhanced dilator 105 will vary based on the outer diameter. The inner diameter may remain constant; thus, the wall thickness may increase as the outer diameter increases. In some embodiments the wall thickness may range from 0.056"-0.059". The shaft may comprise a reinforcing member 34 which is surrounded by one or more polymer layers. The reinforcing member 34 provides stiffness to the assembly; this stiffness supports the flexible puncturing device during puncture. Additionally, the reinforcing member 34 provides support to the specialty therapy sheath during puncture and while crossing the septum. This is an advantage over what is currently used in the field, as currently, less stiff dilators comprised of a softer polymer material are used. These dilators lack the support for puncturing and crossing the septum. Furthermore, due to the softer material, skiving may occur, which creates particulates within the inner lumen. These particulates may be released into the body during the procedure which increases the risk of embolisms. The reinforcing member 34 enables the enhanced dilator 105 to be shaped either prior or during the procedure. The shapeability of the enhanced dilator 105 provides physicians with improved positioning on the septum while also providing increased reach of the distal tip (i.e., increased distal tip distance). Alternatively, the physician is able to withdraw the enhanced dilator 105 from the system and shape the enhanced dilator 105 to a desired curvature and reinsert the enhanced dilator 105. Alternatively, physicians may induce the curvature prior to the procedure. Thus, the example workflow, described above, may include an additional step of shaping the enhanced dilator 105 either prior to the start of the procedure or at any time during the puncture. The proximal end of the enhanced dilator 105 comprises a handle 201. The handle 201 comprises a hub 202 that is operable to be coupled to the hub of the specialty sheath.

In some embodiments, the hub 202 of the enhanced dilator 105 comprises a resilient coupling system 229. The resilient coupling system 229 provides the additional benefit of detachably coupling with a specialty therapy sheath with large or unknown manufacturing tolerances. As the resilient coupling system 229 of the dilator hub 202 couples to the sheath hub of the specialty therapy sheath, the enhanced dilator 105 and the therapy sheath can be manipulated and handled by the physician as a single device. This allows for greater control of the enhanced dilator 105 and specialty therapy sheath when advancing to the SVC or right atrium 906 and during the positioning on the fossa ovalis 908. One the puncturing is complete, the enhanced dilator 105 and therapy sheath cross the septum 912, 914. Once the therapy sheath has crossed the septum, the enhanced dilator 105 is uncoupled from the therapy sheath. When uncoupled, the therapy sheath and enhanced dilator 105 act as two separate devices and the enhanced dilator 105 may be withdrawn with the flexible puncturing device 916 leaving the therapy sheath in the left atrium. Once the enhanced dilator 105 and flexible puncturing or perforation device 110 are removed, the therapy device may be inserted into the therapy sheath and the therapeutic procedure may commence. As such, in some embodiments, the systems of the present invention provide a workflow that may reduce the number device exchanges, facilitate repeatability, improve the coupling of the dilator and sheath, provide adequate anchoring and enhance safety.

Figure 12A:
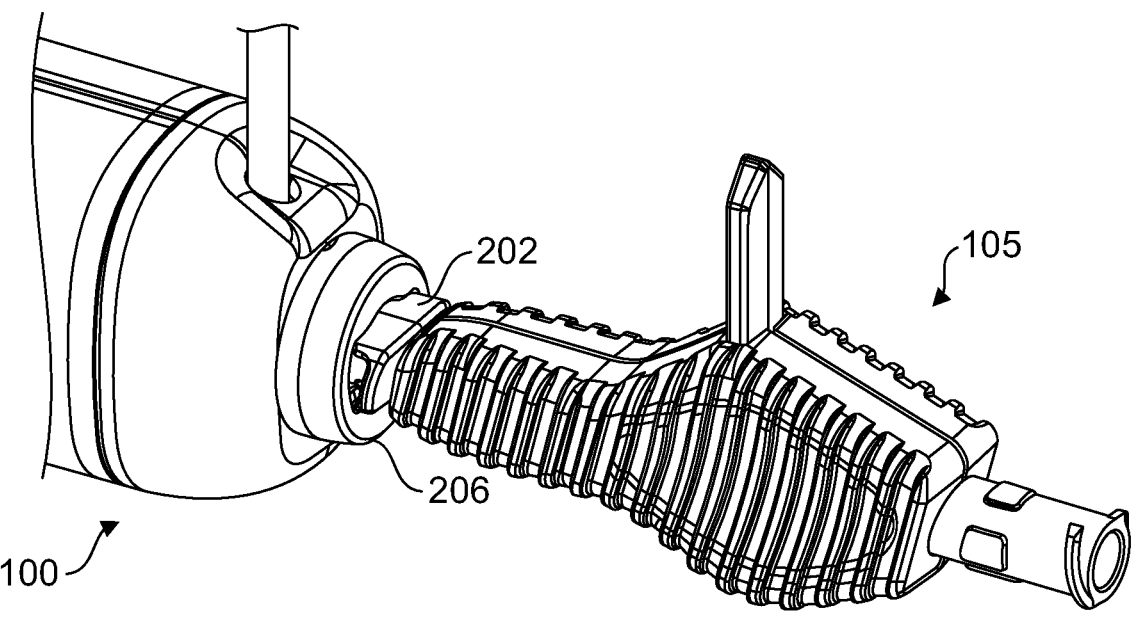
FIGS. 12A and 12B are perspective views of a dilator inserted into a sheath and a dilator hub engaging a sheath hub according to embodiments of the invention.
Figure 12B:
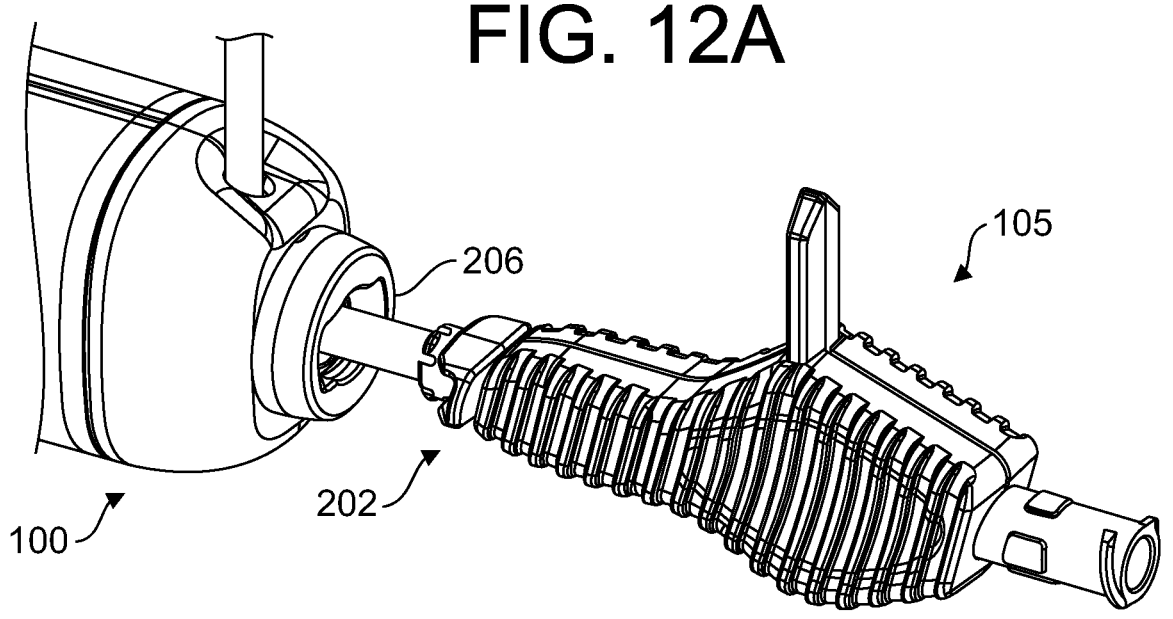

FIGS. 12A and 12B are perspective views of a dilator 105 and sheath 100 having a mechanism to prevent or inhibit relative rotation between the dilator 105 and the sheath 100. FIGS. 12A and 12B illustrate the dilator 105 inserted into a sheath such that the dilator hub 202 is engaging with the sheath hub (FIG. 12A) and the dilator 105 partially inserted into a sheath (FIG. 12B) according to embodiments of the invention. As shown, the dilator hub 202 is adapted to mate with the sheath hub 206 when the dilator is fully inserted into the sheath. The hub 202 and 206 are shaped so as to inhibit or prevent relative rotation of the dilator 105 with respect to the sheath 100. As shown in FIG. 12A, the tapered surfaces on the hubs 202, 206 will guide the dilator hub 202 into the proper engagement orientation upon insertion into the sheath hub 206.

Figure 13A:
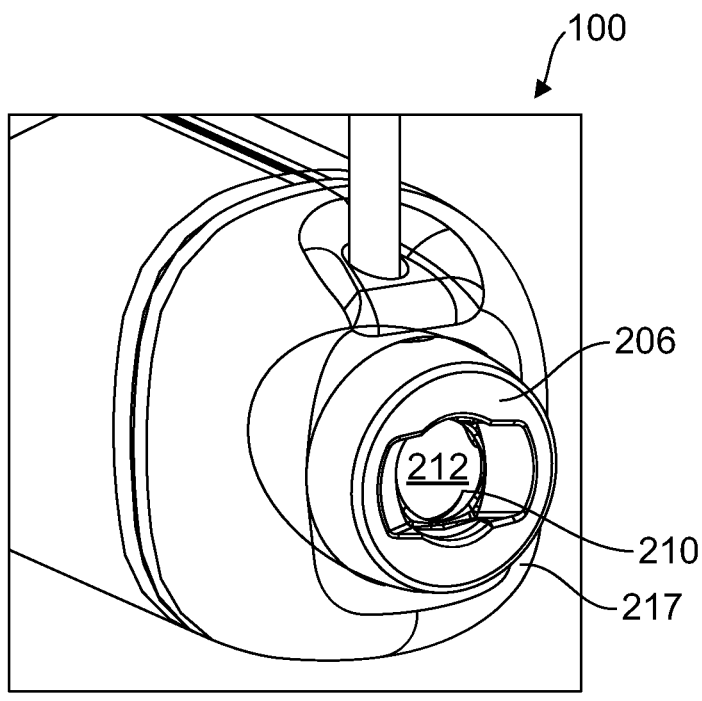
FIG. 13A is a perspective view of a sheath hub and FIG. 13B is a plan view of a portion of a dilator hub mating with a sheath hub according to embodiments of the invention.
Figure 13B:
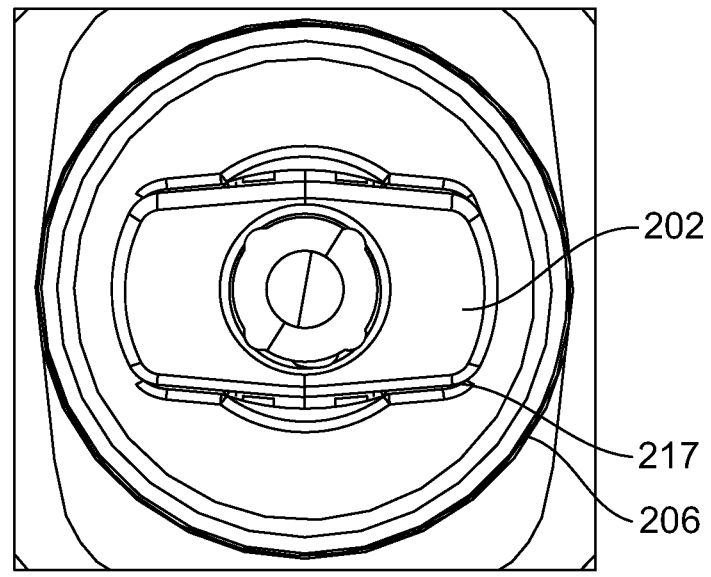

FIG. 13A is a perspective view of a sheath hub and FIG. 13B is a plan view of a portion of a dilator hub mating with a sheath hub according to embodiments of the invention. As shown in FIG. 13A, the sheath hub 206 has a generally rectangular opening 210 surrounding a lumen 212 adapted to accept the dilator shaft. As shown in FIG. 13B, upon longitudinal insertion of the dilator 105 into the sheath, the dilator hub 202 has an outer surface 216 shaped to mate with and contact the opening 210 in the sheath hub 206. In this mated configuration, the mating surfaces 217 of the opening 210 and the outer surface 216 contact each other, which prevent relative rotation of the components. In various embodiments the opening 210 has a tapered or funnel shape in the axial direction. Additionally, the opening 210 may include one or more curved edge.

Figure 14A:
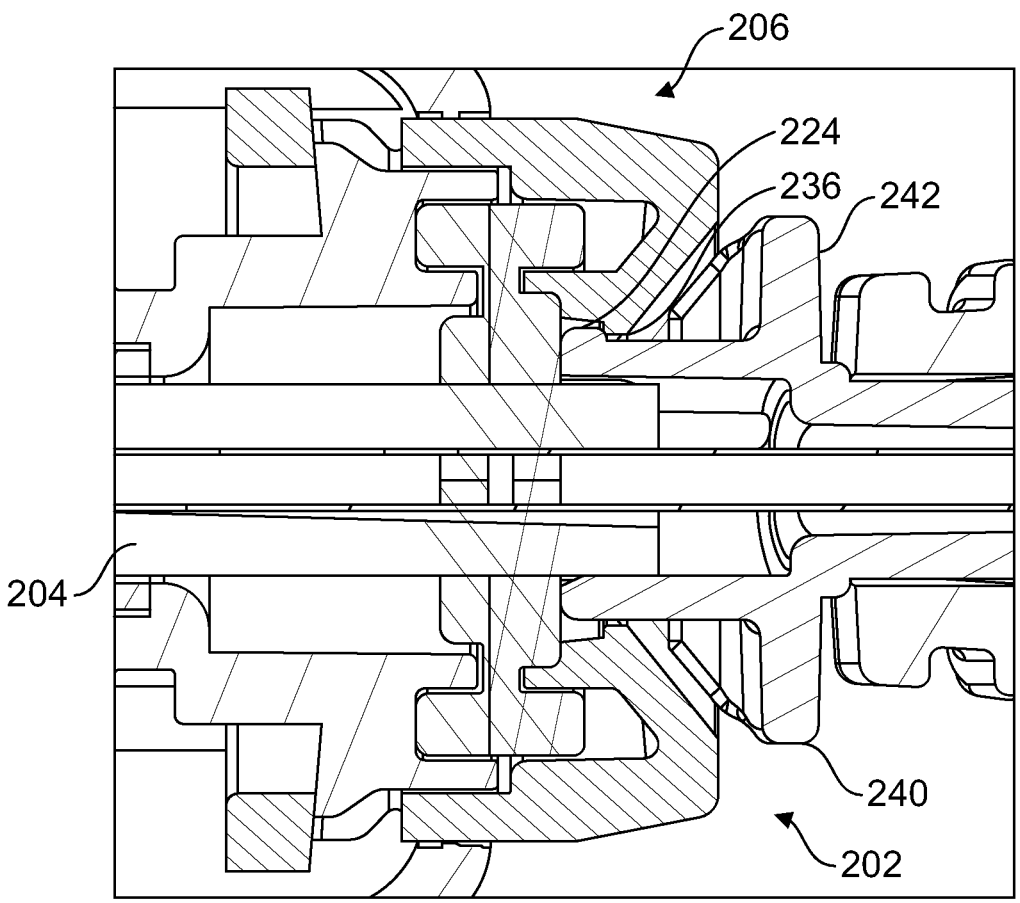
FIG. 14A is a sectional view of a dilator hub mating with a sheath hub and FIG. 14B is a perspective view of a dilator hub according to embodiments of the invention.
Figure 14B:
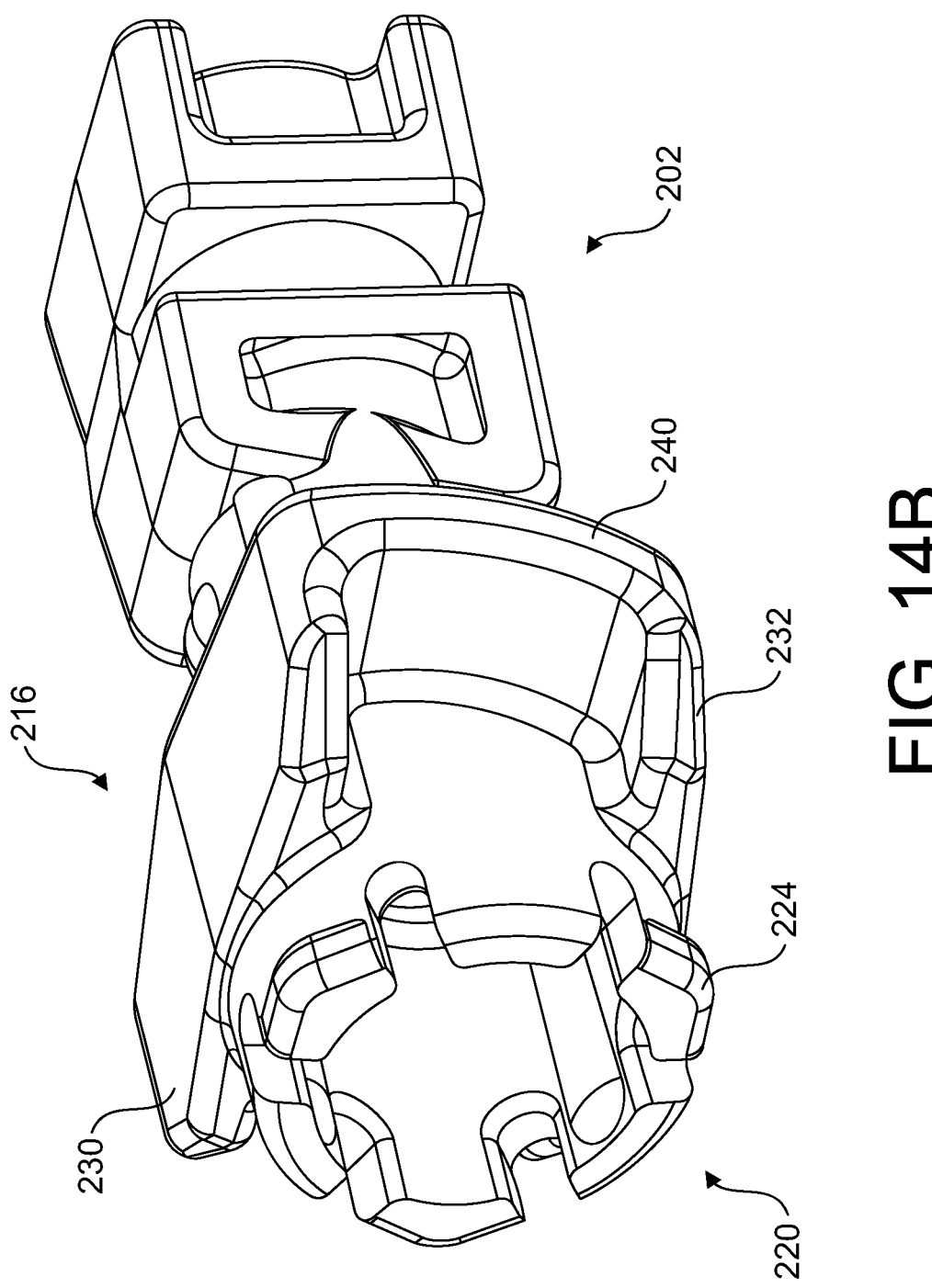

FIG. 14A is a sectional view of a dilator hub mating with a sheath hub and FIG. 14B is a perspective view of a dilator hub according to embodiments of the invention. As shown in FIG. 14A, the dilator is fully inserted into the sheath, such that the dilator hub 202 is fully engaged with the sheath hub 206. In FIG. 14B, the dilator shaft is omitted to better show internal features of the dilator hub 202. As shown, the distal end of the dilator hub 202 includes an axial lock feature 220, which includes a series of circumferentially disposed protrusions 224. As shown in FIG. 14A, these protrusions 224 are adapted to engage with corresponding shoulders 236 on the sheath hub 206. The interaction between the protrusions 224 and the shoulders 236 creates a resistance to an axial disengagement force, such that the dilator hub 202 is secured axially within the sheath hub 206. The dilator hub 202 further includes opposing longitudinal surfaces 230 and 232, which extend along the longitudinal axis of the hub, and opposing lateral surfaces 240 and 242, which extend radially outward and generally perpendicular to the longitudinal axis. As shown in FIG. 14A, when the dilator hub 202 mates with the sheath hub 206, opposing longitudinal surfaces 230 and 232 engage with corresponding surfaces of the sheath hub, so as to resist or prevent relative rotation. The corresponding may be inner portions of opening 210.

Figure 15A:
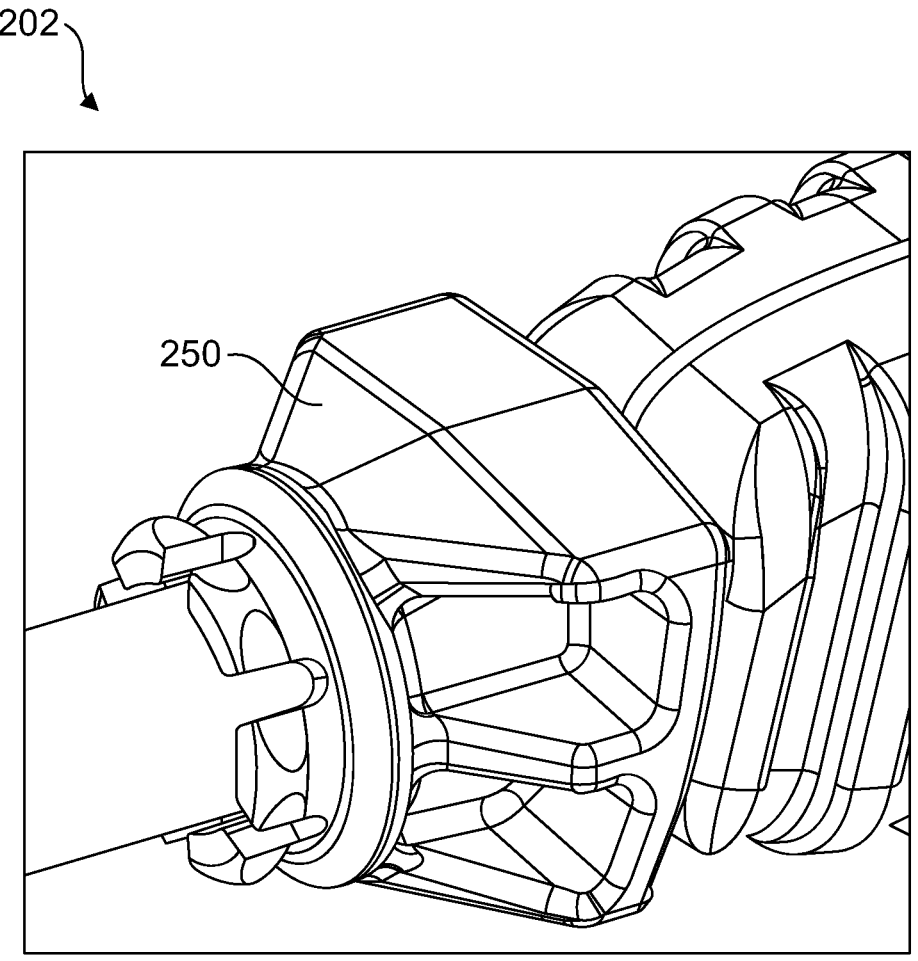
FIG. 15A is a perspective view of a dilator hub and FIG. 15B is a sectional view of a dilator hub mating with a sheath hub according to embodiments of the invention.
Figure 15B:
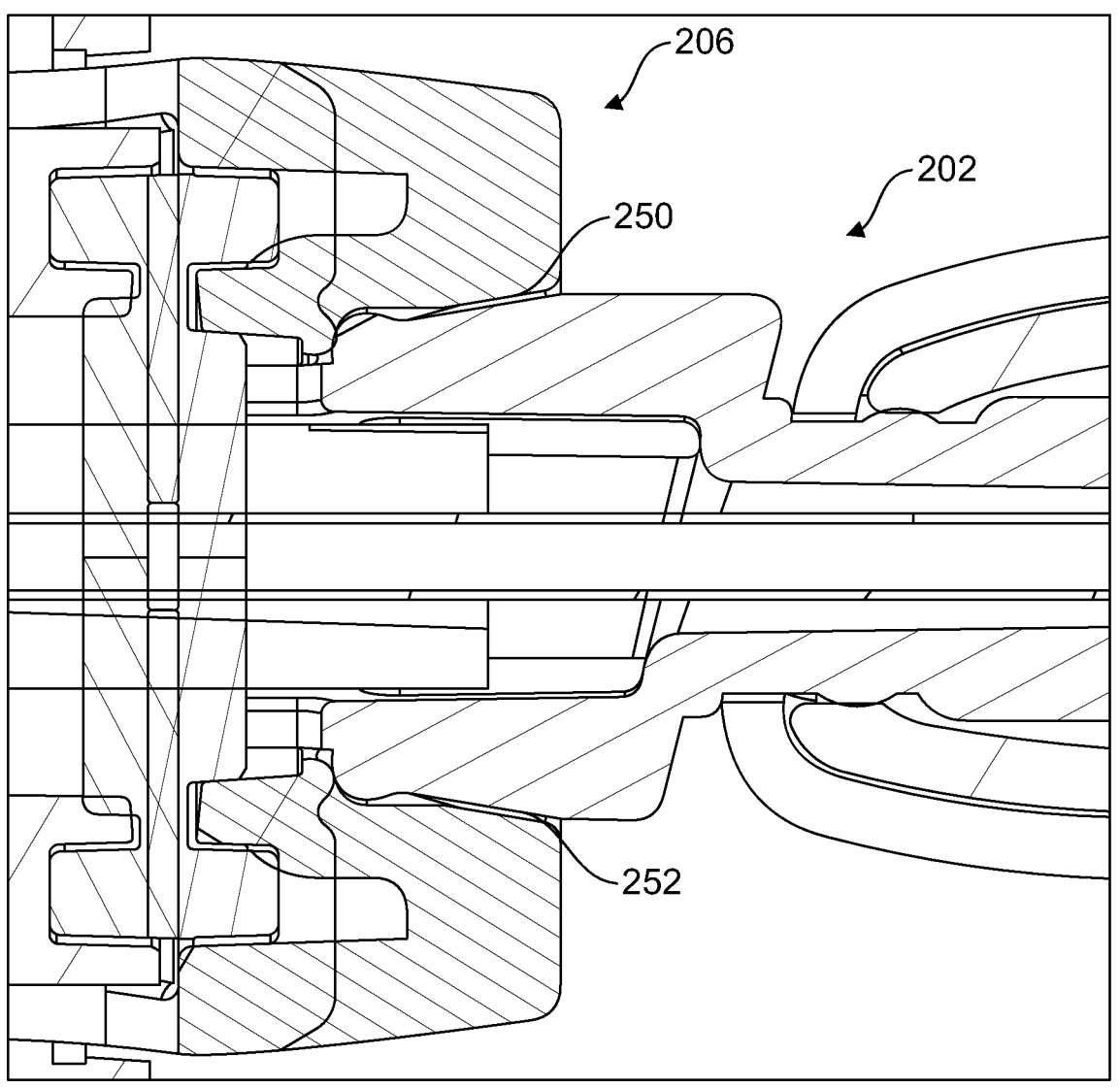

FIG. 15A is a perspective view of a dilator hub and FIG. 15B is a sectional view of a dilator hub mating with a sheath hub according to embodiments of the invention. As shown, the dilator hub 202 includes an angled disengagement surface 250. This surface 250 mates with a corresponding surface 252 on the sheath hub 206. The two surfaces may have slightly different angles or share a common angle but be positioned not parallel to the axis of the dilator, such that upon rotation of the dilator hub 202, the surface 252 generates an axial force upon the disengagement surface 250. This axial force causes disengagement of the dilator hub 202 from the sheath hub 206. By changing the angles of these surfaces, the amount of torque and the degree of rotation required for disengagement may be adjusted.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A dilator for facilitating access to a patient's heart and for coupling with a sheath including a sheath hub, the dilator comprising:
   a dilator shaft defining a lumen adapted to receive and support a puncturing device, the dilator shaft including a proximal portion for manipulation by a user and a distal portion for placement in or near the heart for manipulation by a user; and
   a hub coupled to the proximal portion of the dilator shaft, the hub including a cylindrical body having a hexagonal distal end and an angled proximal end, the hub including a rotational coupling structure for coupling to the sheath hub so as to inhibit relative rotation between the dilator and the sheath, wherein the rotational coupling structure comprises a resilient coupling system comprising the hexagonal distal end including flat portions and rounded edges for contacting an inner surface of the sheath hub.

2. The dilator of claim 1 wherein the sheath is a therapy sheath.

3. The dilator of claim 1 wherein the puncturing device is an RF puncturing device.

4. The dilator of claim 1 wherein the rotational coupling structure includes a protrusion adapted to mate with a recess in the sheath hub.

5. The dilator of claim 1 wherein the dilator hub includes an angled disengagement surface adapted to contact a mating surface on the sheath hub, the mating surface being configured to generate an axial disengagement force upon the disengagement surface.

6. The dilator of claim 5, wherein the angled disengagement surface includes a first surface that is not parallel to a second surface associated with the mating surface.

7. The dilator of claim 1, wherein the shaft includes a reinforcing member.

8. The dilator of claim 1, wherein the distal portion includes one or more radiopaque markers.

9. The dilator of claim 1, wherein the rotational coupling structure includes a first surface configured to contact a first surface of a recess located on the sheath hub.

10. The dilator of claim 9, wherein the rotational coupling structure includes a second surface configured to contact a second surface of the recess located on the sheath hub.

11. An enhanced dilator for coupling with a therapy sheath having a sheath hub, the enhanced dilator comprising:
   a dilator shaft defining a lumen for receiving a puncturing device therethrough, the dilator shaft being structured to provide support for the puncturing device when the puncturing device is used to create a puncture in a tissue, the dilator shaft having a proximal portion and a distal portion; and
   a dilator hub connected to the proximal portion of the dilator shaft, the dilator hub including a cylindrical body having a hexagonal distal end and an angled proximal end, the hub including a resilient coupling system for coupling to the sheath hub, wherein the resilient coupling system comprises the hexagonal distal end including flat portions and rounded edges for contacting an inner surface of the sheath hub.

12. The enhanced dilator of claim 11, wherein the hexagonal distal end is made of a resilient material, wherein gaps formed between the flat portions and the inner surface of the sheath hub provides space into which the resilient material may deflect.

13. The enhanced dilator of claim 11, wherein the dilator shaft includes a reinforcing member for supporting a flexible puncture device.

14. The enhanced dilator of claim 11, wherein the distal portion includes a radiopaque marker.

15. The enhanced dilator of claim 11, wherein the resilient coupling system includes a cylindrical body having an angled proximal end.

16. The enhanced dilator of claim 11, wherein the resilient coupling system includes a plurality of circumferentially disposed protrusions.

17. A system for facilitating access to a patient's heart, the system comprising:
   a dilator including a shaft defining a lumen adapted for receiving and supporting a puncturing device, the shaft including a proximal portion for manipulation by a user and a distal portion for placement in or near the heart for manipulation by a user;
   a dilator hub coupled to the proximal portion of the dilator shaft, the dilator hub including a cylindrical body having a hexagonal distal end and an angled proximal end, the hub including a rotational coupling structure, wherein the rotational coupling structure comprises a resilient coupling system comprising the hexagonal distal end including flat portions and rounded edges;
   a sheath including a sheath body defining a lumen adapted for receiving the dilator; and
   a sheath hub coupled to a proximal portion of the sheath body, the sheath hub including a recess for coupling with the rotational coupling structure to inhibit relative rotation between the dilator and the sheath.

18. The system of claim 17, wherein the hexagonal distal end is made of a resilient material, wherein gaps formed between the flat portions and the inner surface of the sheath hub provides space into which the resilient material may deflect.

19. The system of claim 17, wherein the recess includes a generally rectangular shape surrounding the lumen adapted for receiving the dilator.

20. The system of claim 17, wherein the rotational coupling structure includes a first surface configured to contact a first inner portion of the recess and a second surface configured to contact a second inner portion of the recess.

* * * * *